United States Patent
Barbera et al.

(10) Patent No.: US 12,258,275 B2
(45) Date of Patent: Mar. 25, 2025

(54) ELASTOMER COMPOSITIONS COMPRISING AN ADDUCT BETWEEN AN SP2 HYBRIDIZED CARBON ALLOTROPE AND A DICARBOXYLIC ACID DERIVATIVE

(71) Applicant: PIRELLI TYRE S.p.A., Milan (IT)

(72) Inventors: Vincenzina Barbera, Milan (IT); Maurizio Galimberti, Milan (IT); Attilio Citterio, Milan (IT); Gabriella Leonardi, Milan (IT); Roberto Sebastiano, Milan (IT); Jiemeng Li, Milan (IT)

(73) Assignee: PIRELLI TYRE S.p.A., Milan (IT)

( * ) Notice: Subject to any disclaimer, the term of this patent is extended or adjusted under 35 U.S.C. 154(b) by 678 days.

(21) Appl. No.: 17/594,564

(22) PCT Filed: Apr. 27, 2020

(86) PCT No.: PCT/IB2020/053921
§ 371 (c)(1),
(2) Date: Oct. 22, 2021

(87) PCT Pub. No.: WO2020/222103
PCT Pub. Date: Nov. 5, 2020

(65) Prior Publication Data
US 2023/0002235 A1    Jan. 5, 2023

(30) Foreign Application Priority Data
Apr. 29, 2019    (IT) .................. 102019000006435

(51) Int. Cl.
B32B 9/00    (2006.01)
C01B 32/159    (2017.01)
(Continued)

(52) U.S. Cl.
CPC .......... *C01B 32/21* (2017.08); *C01B 32/159* (2017.08); *C01B 32/174* (2017.08);
(Continued)

(58) Field of Classification Search
CPC ..... Y10T 428/30; B82Y 30/00; C01B 32/159; C01B 32/174; C01B 32/194;
(Continued)

(56) References Cited

U.S. PATENT DOCUMENTS

2006/0155376 A1    7/2006 Asgari
2007/0196262 A1    8/2007 Billups et al.
(Continued)

FOREIGN PATENT DOCUMENTS

WO         2013/130099 A1    9/2013
WO    WO 2016/050887 A1    4/2016
WO    WO 2018/087685 A1    5/2018

OTHER PUBLICATIONS

International Search Report form the European Patent Office in corresponding International Application No. PCT/IB2020/053921 mailed Jun. 24, 2020.
(Continued)

*Primary Examiner* — Daniel H Miller
(74) *Attorney, Agent, or Firm* — Finnegan, Henderson, Farabow, Garrett & Dunner, L.L.P.

(57) ABSTRACT

The present invention relates to elastomer compositions comprising adducts between compounds of formula (I) preferably derived from natural sources such as mucic, pyromucic, glucaric, glycaric, galactaric, muconic acid and/or linear derivatives thereof containing ester or amide groups and/or cyclic derivatives thereof with heteroatoms in the ring, such as oxygen or nitrogen, and carbon allotropes in which the carbon is $sp^2$ hybridized, such as for example carbon nanotubes, graphene or nanographites, carbon black.

12 Claims, 15 Drawing Sheets

(51) Int. Cl.
| | |
|---|---|
| C01B 32/174 | (2017.01) |
| C01B 32/194 | (2017.01) |
| C01B 32/198 | (2017.01) |
| C01B 32/21 | (2017.01) |
| C07D 309/38 | (2006.01) |
| C09C 1/56 | (2006.01) |
| B82Y 30/00 | (2011.01) |

(52) U.S. Cl.
CPC .......... *C01B 32/194* (2017.08); *C01B 32/198* (2017.08); *C07D 309/38* (2013.01); *C09C 1/56* (2013.01); *B82Y 30/00* (2013.01); *C01B 2202/02* (2013.01); *C01B 2202/06* (2013.01); *C01B 2204/04* (2013.01); *C01P 2002/74* (2013.01); *C01P 2002/82* (2013.01); *C01P 2002/84* (2013.01); *C01P 2002/86* (2013.01); *C01P 2004/04* (2013.01)

(58) Field of Classification Search
CPC .............. C01B 32/198; C01P 2202/02; C01P 2202/06; C01P 2202/04
USPC ........................................................ 428/408
See application file for complete search history.

(56) References Cited

U.S. PATENT DOCUMENTS

| | | |
|---|---|---|
| 2015/0191579 A1 | 7/2015 | Wampler et al. |
| 2017/0275169 A1 | 9/2017 | Galimberti et al. |
| 2020/0055820 A1 | 2/2020 | Galimberti et al. |

OTHER PUBLICATIONS

Written Opinion of the International Searching Authority from the European Patent Office in corresponding International Application No. PCT/IB2020/053921 mailed Jun. 24, 2020.
Diani, J. et al., "A review on the Mullins effect", HAL open science, European Polymer Journal 45, 2009, pp. 601-612.
Bohm, G.A. et al., "Furthering the understanding of the non linear response of filler reinforced elastomers", Polymer 51, 2010, pp. 2057-2068.
Galimberti, M. et al., "The Role of CNTs in Promoting Hybrid Filler Networking and Synergism with Carbon Black in the Mechanical Behavior of Filled Polyisoprene", Macromolecular Journals, Macromolecular Materials and Engineering, 2013, pp. 241-251.
Rahmat, M. et al., "Carbon nanotube-polymer interactions in nanocomposites: A review", Composites Science and Technology, 72, 2011, pp. 72-84.
Galimberti, M. et al., "Filler Networking of A Nanographite With A High Shape Anisotropy And Synergism With Carbon Black In Poly(1,4-Cis-Isoprene)-Based Nanocomposites" Rubber Chemistry and Technology, vol. 87, No. 2, pp. 197-218, 2014.
Potts, J. R. et al., "Graphene-based polymer nanocomposites." Polymer 52, pp. 5-25, 2011.
Matos, C. et al., "Multifunctional materials based on iron/iron oxide-filled carbon nanotubes/natural rubber composites", Elsevier, Carbon 50, pp. 4685-4695, 2012.
Wang, M.J. et al., "New Generation Carbon-Silica Dual Phase Filler Part I. Characterization and Application to Passenger Tire", Rubber Chemistry and Technology, vol. 75, pp. 247-263, 2002.
Wang, M.J. et al., "Carbon-Silica Dual Phase Filler, a New Generation Reinforcing Agent for Rubber", KGK Kautschuk Gummi Kunststoffe, 51, Jahrgang, pp. 348-360, 1998.
Wang, W. et al., "Study of Surface Activity of Carbon Black by Inverse Gas Chromatography, Part III: Superficial Plasma Treatment of Carbon Black and its Surface Activity", KGK Kautschuk Gummi Kunstatoffe 46, Jahrgang, pp. 933-940, 1993.
Kinney, C. R. et al., "Ozonization Studies of Coal Constitution", Chem. Soc., vol. 74, pp. 57-61, Jan. 5, 1952.
Cataldo, F., "Ozone Reaction with Carbon Nanostructures 2: The Reaction of Ozone with Milled Graphite and Different Carbon Black Grades", Journal of Nanoscience and Nanotechnology, American Scientific Publishers, vol. 7, pp. 1446-1454, 2007.
Chen, J. et al., "An improved Hummers method for eco-friendly synthesis of graphene oxide", Elsevier Ltd., Carbon 64, pp. 225-229, 2013.
Marcano, D.C. et al., "Improved Synthesis of Graphene Oxide", AC Nano, vol. 4, No. 8, pp. 4806-4814, 2010, www.acsnano.org.
Kovtyukhova, N.I. et al., "Layer-by-Layer Assembly of Ultrathin Composite Films from Micron-Sized Graphite Oxide Sheets and Polycations", Chem. Mater. 11, pp. 771-778, 1999.
Guerrero-Contreras, J. et al., "Graphene oxide powders with different oxidation degree, prepared by synthesis variations of the Hummers method", Materials Chemistry and Physics 153, Elsevier, pp. 209-220, 2015.
Eda, G. et al., "Large-area ultrathin films of reduced graphene oxide as a transparent and flexible electronic material", Materials Science and Engineering, Nature Nanotechnol, vol. 3, pp. 270-274, 2008.
You, F. et al., "In situ thermal reduction of graphene oxide in a styrene-ethylene/butylene—styrene triblock copolymer via melt blending", 2013 Society of Chemical Industry, Polym Int, vol. 63, 93-99, 2014.
Posudievsky, O.Y. et al., "Preparation of graphene oxide by solvent-free mechanochemical oxidation of graphite", The Royal Society of Chemistry, Journal of Materials Chemistry, vol. 22, pp. 12465-12467, 2012.
Potts, J.R. et al., "Processing-Morphology-Property Relationships and Composite Theory Analysis of Reduced Graphene Oxide/Natural Rubber Nanocomposites", American Chemical Society, Macromolecules, vol. 45, pp. 6045-6055, 2012.
Singh, P. et al., "Organic functionalization and characterization of single-walled carbon nanotube", Chemical Society Reviews, The Royal Society of Chemistry 2009, vol. 38, pp. 2214-2230, 2009.
Bilalis, P. et al., "Non-covalent functionalization of carbon nanotubes with polymers", RSC Advances, The Royal Society of Chemistry 2014, vol. 4, pp. 2911-2934, 2014.
Tummala, N. R. et al., "SDS Surfactants on Carbon Nanotubes: Aggregate Morphology" AC Nano, vol. 3, No. 3, pp. 595-602, 2009.
Liu, Y. et al., "Decoration of carbon nanotubes with chitosan" Elsevier, Carbon 43, pp. 3178-3180, 2005.
Galimberti, M. et al., "Supramolecular interactions of carbon nanotubes with biosourced polyurethanes from 2-(2,5-dimethyl-1H-pyrrol-1-yl)-1,3-propanediol", Elsevier Ltd., Polymer, vol. 63, pp. 62-70, 2015.
Galimberti, M. et al., "Innovative Chemicals from Bio-sourced C3 and C6 Building Blocks", CPAC Rome Workshop 2019, Rome (I), 33 pgs., 2019.
Notification of the First Office Action issued by the China National Intellectual Property Administration on Dec. 26, 2023, in corresponding Application No. CN 202080031963.1 (6 pages).
Irvine, N. M. et al., "Characterization of two hydroxytrichloropicolinic acids: application of the one-bond chlorine-isotope effect in $^{13}$C NMR", Magnetic Resonance in Chemistry, 2008, vol. 46, Issue 5, pp. 436-440, 3 pages.
Ning, N. et al., "Design and preparation of carbon black/carbon nanotubes/silicone elastomer composites with high elasticity and high electrical conductivity stability", Science China Press, 2018, vol. 63, Issue 34, pp. 3677-3686.
Galimberti, M. et al., Innovative Chemicals from Bio-sourced C3 and C6 Building Blocks, CPAC Rome Workshop 2019, Rome (I), Mar. 25-27, 2019, pp. 1-66.

ELASTOMER COMPOSITIONS COMPRISING AN ADDUCT BETWEEN AN SP2 HYBRIDIZED CARBON ALLOTROPE AND A DICARBOXYLIC ACID DERIVATIVE

The present invention relates to adducts comprising carbon allotropes and unsaturated or saturated diacids and linear and/or cyclic derivatives thereof, as components for producing crosslinkable elastomer compositions.

The invention relates in particular to adducts comprising compounds preferably derived from natural sources such as mucic, pyromucic, glucaric, glycaric, galactaric acids, muconic acid and/or linear derivatives thereof containing ester or amide groups and/or cyclic derivatives thereof with heteroatoms in the ring, such as oxygen or nitrogen, and carbon allotropes in which the carbon is $sp^2$ hybridized, such as for example carbon nanotubes, graphene or nanographites, carbon black, for the purpose of improving the physicochemical characteristics of said allotropes mainly by increasing their dispersibility and the stability of their interactions in polymer matrices, such as for example crosslinkable elastomer compositions, and in liquid media.

The nanometric $sp^2$ carbon allotropes such as graphene, nanographites consisting of a small number of graphene layers (from a few units to a few tens), graphite, single-wall or multi-walled carbon nanotubes, are characterized by a high aspect ratio, i.e. by a high ratio of their larger dimension to their smaller dimension. It is known that on increasing the aspect ratio, the area per unit volume increases. Thus, these allotropes are nano-objects and have a high aspect ratio: they have a very large surface area.

The aforementioned carbon allotropes, produced in the laboratory or on an industrial scale, do not in fact consist of carbon alone. On their surface there are functional groups, typically oxygenated, produced during synthesis. However, these functional groups are present in a very small amount, so small that they: (i) are difficult to identify, for example by analyses such as infrared spectroscopy; (ii) do not alter the solubility parameter of the $sp^2$ carbon allotrope; (iii) do not give rise to chemical reactions and therefore to chemical bonds in observable amounts, with other substances present in the mixture in which the allotropes are located; (iv) do not give rise to chemical reactions and therefore to chemical bonds in observable amounts with the polymer matrix in which the allotropes are located.

It would instead be highly desirable to have, on the surface of the $sp^2$ carbon allotropes, functional groups in amounts such as to: (i) alter the solubility parameter of said allotropes; (ii) give rise to chemical reactions with other substances; (iii) give rise to chemical bonds with the polymer matrices in which they are located.

The presence of functional groups on the surface of the $sp^2$ carbon allotropes would be desirable for various applications, for example: (i) elastomer composites for dynamic-mechanical applications, for example in tire compounds; (ii) elastomeric and thermoplastic composites with polymers of a polar nature; (iii) dispersions in liquid media for coating layers.

In fact, the $sp^2$ carbon allotropes, such as carbon black, graphene and nanographites and carbon nanotubes, are used both in polymer, thermoplastic or elastomer matrices, and in liquid dispersions for coating layers. They promote mechanical reinforcement, as well as the thermal and electrical conductivity of the materials in which they are present. Moreover, some carbon allotropes such as carbon nanotubes, graphene and nanographites in polymer matrices have a notable flame-retardant effect. For the reason already mentioned, i.e. the formation of a high interfacial area, the improvement in the aforementioned properties is particularly marked when "nanometric" carbon allotropes are used, such as carbon nanotubes, graphene and nanographites. Moreover, carbon nanotubes and graphene are intrinsically endowed with exceptional mechanical properties, and electrical and thermal conductivity.

The most important application of carbon black is in elastomer compounds, as reinforcing filler, in particular in tire compounds. Carbon black is an excellent reinforcing filler, but is not the ideal filler for reducing the dissipation of energy during a dynamic-mechanical application of an elastomer compound, e.g. for application in tire compounds. In fact, to achieve an effective action of reinforcement of an elastomer matrix, the fillers must be used in appreciable amounts. Typically, the ASTM standard compounds stipulate the use of more than 30 parts of filler per 100 parts of elastomer. At this level, the filler is beyond its percolation threshold, i.e. forms a network. Thus, there are not only filler-polymer interactions, but also filler-filler interactions. These interactions lead to a high value of the viscoelastic modulus in the material not subjected to deformation. These interactions are, however, essentially based on non-bonding forces, typically van der Waals forces. On applying energy to the composite material that contains the reinforcing fillers and gradually increasing the strain amplitude, the reinforcement based on non-bonding interactions is reduced. Thus, there is a reduction of the viscoelastic modulus with increase in the strain amplitude. This phenomenon, for low amplitudes of deformation, is known as the Payne effect and is a source of dissipation of energy. The theory of reinforcement still says that the surface area is the parameter that influences the value of the viscoelastic modulus in the undeformed material. The larger the surface area, the higher the modulus of the undeformed material.

However, elastomeric materials that contain carbon black also show an appreciable reduction of loads for elongations that go beyond the limits of linear viscoelasticity.

This phenomenon is known as the Mullins effect. As stated in J. Diani, B. Fayolle, P. Gilormini, A review on the Mullins effect, European Polymer Journal 45 (2009) 601-612, the Mullins effect becomes more important as the content of carbon black is increased.

The nanometric carbon allotropes are ideal for having a high value of modulus in an undeformed elastomer composite. However, in this case as well, if the interactions that lead to a high value of modulus in the undeformed material are of a supramolecular nature, i.e. are based on van der Waals forces, the modulus declines with deformation and there is dissipation of energy by the Payne effect and/or the Mullins effect.

Ultimately, in the case of carbon allotropes it is not possible to take advantage of the large surface area to have high reinforcement at low strains without at the same time having high dissipation of energy at high strains. This is because the $sp^2$ carbon allotropes do not establish chemical bonds with the polymer chains, not having functional groups on their surface capable of promoting chemical bonding with the polymer chains.

It would thus be highly desirable to be able to establish chemical bonds between the carbon allotropes and polymer matrices, or to have functional groups on the surface of the carbon allotropes capable of establishing such bonds.

The elastomers that are used for tire compounds are mainly poly(1,4-cis-isoprene) (from Hevea brasiliensis and synthetic), poly(1,4-butadiene) (BR rubber), poly(styrene-co-butadiene) (SBR rubber). All these polymers are nonpolar hydrocarbons. Thus, dispersion of the carbon allotropes is not particularly hampered. Nevertheless, it presents considerable technical problems. In the case of carbon black, it requires an appreciable quantity of mechanical energy, which may lead to breaking of the polymer chains, with reduction of the mechanical reinforcement. Moreover, as soon as the mixing process is completed, there is agglomeration of the filler, which leads to formation of the filler network, which will be broken on applying a strain, causing the Payne effect and/or the Mullins effect, or dissipation of energy. This is stated for example in G. A. Bohm, W. Tomaszewski, W. Cole, T. Hogan, Furthering the understanding of the non-linear response of filler reinforced elastomers, Polymer 51 (2010) 2057-2068.

Carbon nanotubes may also be mixed directly with a nonpolar elastomer matrix, by mechanical mixing. In "The Role of CNTs in Promoting Hybrid Filler Networking and Synergism with Carbon Black in the Mechanical Behavior of Filled Polyisoprene" *Macromol. Mater. Eng.*, 298, 241-251 (2012), the nanotubes are mixed with rubber in an internal mixer, utilizing the thermo-mechanical energy of mixing, without any prior chemical modification. However, this leads to fracture of said nanotubes, the length of which is shown to be much less than that of the nanotubes before mixing. Polymer nanocomposites with carbon nanotubes are also described in "Carbon nanotube-polymer interactions in nanocomposites: A review, Composites Science and Technology 72 (2011) 72-84". In both of these publications, images are presented with carbon nanotubes dispersed at the level of the individual nanotubes (more or less fractured) but they also show agglomerates.

A nanographite may also be mixed directly with a nonpolar elastomer matrix, by mechanical mixing. Examples are given in "Filler Networking of A Nanographite With A High Shape Anisotropy and Synergism With Carbon Black In Poly(1,4-Cis-Isoprene)-Based Nanocomposites" Rubber Chemistry and Technology, Vol. 87, No. 2, pp. 197-218 (2014) and in "Graphene-based polymer nanocomposites." Polymer, 52(1), 5-25 (2011)". In these publications too, dispersions are shown with few graphene layers, but also agglomerates. In particular, in Rubber Chemistry and Technology, Vol. 87, No. 2, pp. 197-218 (2014), it is shown how the number of layers stacked in the nanographite aggregates tends to increase in the crosslinked elastomer composite.

The article Carbon 2012, 50, 4685-4695 describes mixing nanotubes with natural rubber in natural rubber latex, modifying the nanotubes with a surfactant such as sodium dodecyl sulfate. However, the surfactant covers the surface of the carbon allotrope, thus reducing its effectiveness.

Thus, the problem of dispersing carbon allotropes of nanometric dimensions in lipophilic matrices at the level of the constituent particles, either the graphene sheet or the single nanotube, is still unresolved or at least not solved completely and satisfactorily.

The $sp^2$ carbon allotropes, both nanometric and nanostructured, are also used in polymer matrices, both elastomeric and thermoplastic, consisting of polymers of a polar nature. These polymers may have a group of a polar nature in one or in all of the repeating units. Examples of polymers with a polar group in every repeating unit are, for example: polyurethanes, polyethers, polyesters, polycarbonates, poly (vinyl esters), poly(vinyl alcohol). Examples of polymers that do not contain a polar group in every repeating unit are, for example: copolymers of ethylene with polar monomers such as for example vinyl acetate, vinyl(alcohol). Other examples of polymers that do not contain a polar group in every repeating unit are the polymers in which the polar group was introduced by a grafting reaction. Examples of these polymers on which the grafting reaction could be carried out are polyolefins, such as poly(ethylene) and poly(propylene), ethylene-propylene copolymers, polymers derived from dienes, on which an anhydride, such as maleic anhydride or itaconic anhydride, has been grafted, or on which an ester such as ethyl maleate has been grafted, or on which a mixture of an anhydride and an ester has been grafted. The dispersibility and the compatibility of the $sp^2$ carbon allotropes in polar polymer matrices would still be better if there were polar functional groups on the surface of said allotropes.

The $sp^2$ carbon allotropes are also used for preparing dispersions in liquid media for making conductive inks, based both on carbon black and carbon nanotubes and graphene or nanographites. It is now important to have water-based inks, especially for reducing the environmental impact. In the case of dispersions in liquid media, the first aim is to obtain stability of said dispersion, to avoid settling of the allotrope. This problem is especially important for carbon allotropes of nanometric dimensions, such as carbon nanotubes, graphene, nanographites that have a higher aspect ratio and larger surface area and thus form a network more easily.

It would therefore certainly be desirable to have at our disposal $sp^2$ carbon allotropes, such as carbon black, carbon nanotubes, graphene and nanographites, that can form stable dispersions in aqueous media.

Some methodologies have already been proposed for introducing polar groups on carbon allotropes.

The oxidation of carbon black dates back to the 19th century. The methods adopted are based on reactions carried out in harsh and dangerous, potentially explosive conditions. Substances such as $HNO_3$ with $KClO_3$, $H_2SO_4/HNO_3$ with $KClO_3$, $H_2SO_4/NaNO_3$ with $KMnO_4$, respectively, are used. Obviously it would be highly desirable not to have to use these methods for oxidizing carbon black. Not only for the critical aspects relating to the reactions, but also because the chemical nature of the carbon substrate is changed considerably, in a substantially uncontrolled way.

So-called co-fuming technology, described for example in M. J. Wang, Y. Kutsovsky, P. Zhang, L. J. Murphy, S. Laube K. Mahmud, Rubber Chemistry and Technology, 75, 247 (2002) and in M. J. Wang, K. Mahmud, L. J. Murphy, & W. J. Patterson, KAUTSCHUK GUMMI KUNSTSTOFFE, 51, 348 (1998), which results in a filler that contains both carbon black and silica: between 3 and 7% of silica on the surface of the carbon black. However, this technology, which consists essentially of using $SiCl_4$ in the production of carbon black, is very energy-consuming and expensive.

Carbon black has also been treated with ozone, as described for example in Wang W., Vidal A., Donnet J. B., Wang M. J., KGK W., KAUTSCHUKGUMMIKUNSTSTOFFE, 46, 933, 1993; C. R. Kinney, L. D Friedman, J. AM. CHEM. SOC. 57, 74 (1952); M. R. Cines, CAN. PAT. 9, 531 (1956); F. Cataldo, JOURNAL OF NANOSCIENCE AND NANOTECHNOLOGY, 7, 1446 (2007). Ozone is, however, a very reactive and hazardous gas.

Carbon black has also been treated with triazoles, as stated in WO 2013/130099.

Carbon black has also been treated with polysulfides, as stated in US 2015/0191579.

The last two methods are carried out with synthetic products from industrial chemistry, derived from the oil sector.

For the oxidation of graphites, methods have been proposed by removal of $NaNO_3$ (J. Chen, B. Yao, C. Li, G. Shi, CARBON. 64, 225 (2013)), using a $H_2SO_4/H_3PO_4$ mixture (D. C. Marcano, D. V. Kosynkin, J. M. Berlin, A. Sinitskii, Z. Sun, A. Slesarev, L. B. Alemany, W. Lu, J. M. Tour, Acs NANO. 4, 4806 (2010)), pre-oxidizing the graphite with $P_2O_5$ and $K_2S_2O_8$ in $H_2SO_4$ (N. I. Kovtyukhova, P. J. Ollivier, B. R. Martin, T. E. Mallouk, S. A. Chizhik, E. V. Buzaneva, A. D. Gorchinskiy, CHEM. MATER. 11, 771 (1999)), changing the concentration of $NaNO_3$ and $KMnO_4$ and the residence times (J. Guerrero-Contreras, F. Caballero-Briones, MATER. CHEM. PHYS. 153, 209 (2015)). These are chemical reactions carried out with critical reagents and leading to substantial changes of the chemical nature of the allotrope.

With regard to the graphene layers, it has been proposed to apply chemical reduction, for example with hydrazine (G. Eda, G. Fanchini, M. Chhowalla, NAT. NANOTECHNOL. 3, 270 (2008)) or thermal (F. You, D. Wang, J. Cao, X. Li, Z.-M. Dang, G.-H. Hu, POLYM. INT. 63, 93 (2014)). However, besides the use of critical substances such as hydrazine, these two treatments are not completely effective and the $sp^2$ structure of the allotrope is damaged to a varying degree.

The oxidation of nanographites has also been carried out by a mechanical-chemical route (O. Yu. Posudievsky, O. A. Khazieieva, V. G. Koshechko, V. D. Pokhodenko, J. MATER. CHEM. 22, 12465(2012)), with an approach that may, however, be difficult to scale industrially.

It was mentioned above that functionalization of $sp^2$ carbon allotropes with polar groups might facilitate their dispersion in elastomer latices. In the case of nanographites, it is stated for example in Potts et al., Macromolecules 2012, 45, 6045-6055 that the graphene sheets are arranged around the particles of natural rubber attaining percolation at a very low content. To obtain this dispersion, a nanographite is oxidized before being dispersed in the natural rubber latex, with the aforementioned technical problems connected with substantial change in the structure of the allotrope.

Functionalization of carbon nanotubes has been carried out both covalently and supramolecularly, as stated in P. Singh, S. Campidelli, S. Giordani, D. Bonifazi, A. Bianco, M. Prato, *CHEM. SOC. REV* 38, 2214 (2009); M. Rahmat, P. Hubert, Carbon, *COMPOSITES SCIENCE AND TECHNOLOGY.* 72, 72, (2011); P. Bilalis, D. Katsigiannopoulos, A. Avgeropoulos, G. Sakellariou, *RSC ADVANCES,* 4, 2911 (2014).

Dispersion of carbon nanotubes in aqueous solvents has been promoted using a surfactant such as sodium dodecyl sulfate, as stated in "SDS Surfactants on Carbon Nanotubes: Aggregate Morphology" ACS Nano, 2009, 3 (3), pp 595-602. In this case, advantage is taken of the interaction between the dodecyl substituent and the allotrope, whereas the salt ensures dispersion in water. In "Decoration of carbon nanotubes with chitosan" Carbon, 43(15), 3178-3180 (2005), dispersion of carbon nanotubes in acidic solutions (pH=5) by preparing the adduct of the carbon nanotubes with chitosan is described. In this case, the interaction between the ammonium cations and the π systems of the nanotubes is exploited. These modifiers reduce the properties of the allotropes, covering them and not contributing at all to the electrical and thermal conductivity of said allotropes.

The modifying reactions given above are largely based on complex chemical syntheses, sometimes critical from the viewpoint of environmental impact and/or with little possibility of being scaled up to an industrial level.

Moreover, they are not carried out starting from ingredients from renewable sources.

Modification of $sp^2$ carbon allotropes with pyrrole compounds is described in WO 2016/050887 A1 and WO 2018/087685, in the name of the applicants. In particular, there is mention of pyrrole compounds derived from serinol, which is also obtainable from glycerol and is therefore, potentially, an ingredient of natural origin.

The Applicants tackled the problem of carrying out the functionalization of $sp^2$ carbon allotropes, i.e. of preparing adducts between the $sp^2$ carbon allotropes and molecules containing functional groups, in which there is an interaction as stable as possible between said functional groups and the carbon substrate, without substantially altering the structure of said substrate, and primarily the $sp^2$ nature of the carbon atoms.

It would be desirable, moreover, to carry out the interaction between the functional groups and the carbon substrate without using harmful, toxic ingredients.

It would also be desirable to carry out the interaction between the functional groups and the carbon substrate without using solvents and catalysts.

It would also be desirable to be able to use, for the functionalization, substances from natural sources, so as to achieve a low environmental impact.

It would be desirable, moreover, for the functionalization reaction to have high efficiency with various types of $sp^2$ carbon allotropes, such as for example carbon black, graphene and nanographites, carbon nanotubes.

It would be desirable, moreover, for the adducts obtained, i.e. the functionalized $sp^2$ carbon allotropes, to be usable for preparing stable dispersions in liquid media, in particular in an aqueous environment, i.e. dispersions that maintain their characteristics over time and are easy to produce.

It would be desirable, moreover, for the adducts obtained, i.e. the functionalized $sp^2$ carbon allotropes, to be usable for preparing optimal, stable dispersions in polymer matrices, of a nonpolar and/or polar nature, such as for example elastomer compositions, reducing the interaction between particles of the allotrope and maximizing the interaction with the matrix.

The Applicants found that the aforementioned aims may be achieved by means of adducts comprising $sp^2$ hybridized carbon allotropes and unsaturated or saturated diacids, and linear and/or cyclic derivatives thereof.

Surprisingly, the applicants also found that adducts between $sp^2$ hybridized carbon allotropes and unsaturated or saturated diacids, and linear and/or cyclic derivatives thereof, can be dispersed more effectively than expected in elastomer matrices, forming a stable interaction with them. The elastomer compositions thus obtained show low hysteresis and a reduced Payne effect, with consequent reduced dissipation of energy.

Thus, according to a first aspect, the invention relates to an adduct of an $sp^2$ hybridized carbon allotrope and a compound of formula (I)

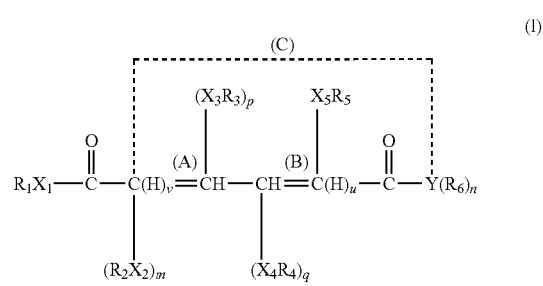

in which the compound of formula (I) may be linear or cyclic and the symbol (C) does not represent a bond when the compound is linear and represents a bond when the compound is cyclic, and $X_1, X_2, X_3, X_4, X_5$ are selected independently from the group consisting of O, N—$R_7$, halogen and S;

and in which if $X_1, X_2, X_3, X_4, X_5$ are halogen, $R_1, R_2, R_3, R_4, R_5$ are absent;

and in which:
  the compound of formula (I) is linear when:
    m and n are 1 and Y is selected from the group consisting of O, N—$R_7$ and S; or
    m is 1 and n is 0 and Y is halogen and
  wherein whenever the compound is linear, the symbols (A) and (B) represent independently a single or a double bond, and
    if the symbols (A) and (B) are a double bond, v, u, p and q are 0;
    if the symbols (A) and (B) are a single bond, v, u, p, q are 1;
    if the symbol (A) is a double bond and the symbol (B) is a single bond, v and p are 0 whereas u and q are 1;
    if the symbol (B) is a double bond and the symbol (A) is a single bond, v and p are 1 whereas u and q are 0;
  the compound of formula (I) is cyclic when:
    the symbol (A) and/or (B) are a double bond, and
    m, v, p, q and u are 0, and
    if Y is O, n is 0, or if Y is N, n is 1;
and in which:
if $X_1$ and Y are $NR_7$ or S, then:
  $R_1$, $R_6$ are selected independently from the group consisting of: hydrogen, linear or branched $C_1$-$C_5$ alkyl, linear or branched $C_2$-$C_5$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;
if $X_1$ and Y are O, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

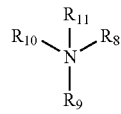

in which $R_8$, $R_9$, $R_{10}$, $R_{11}$ are selected independently from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;
if $X_2, X_3, X_4, X_5$ are O, $NR_7$ or S, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;
  $R_2, R_3, R_4, R_5$ are selected independently from the group consisting of: hydrogen, $C_2$-$C_6$ acyl, linear or branched $C_1$-$C_6$ alkyl, $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

In this way, an adduct is obtained containing $sp^2$ hybridized carbon allotropes that are dispersible in numerous matrices, and are usable in processes in which it is necessary to maintain the characteristics of said allotropes.

In a second aspect, the present invention relates to an elastomer composition comprising an adduct between an $sp^2$ hybridized carbon allotrope and a compound of formula (I)

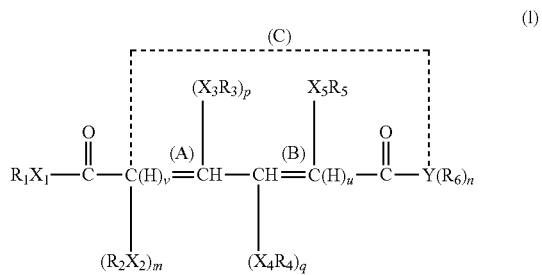

(I)

where the groups $R_1$-$R_6$, $X_1$-$X_5$, Y, and the symbols A, B, C, m, n, p, q, U, V, have the meanings described above.

The compound of formula (I) may be in the form of a salt when: if $X_1$ and Y are O, then $R_1$ and $R_6$ are alkali metals, alkaline-earth metals, transition metals, or

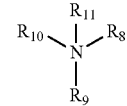

Preferably said alkali metals are selected from the group consisting of lithium, sodium, potassium.

Preferably said alkaline-earth metals are selected from the group consisting of magnesium, calcium.

Preferably said transition metals are rare earths, preferably neodymium.

Preferably the compound of formula (I) is represented by one of the following general formulas from (II) to (VII):

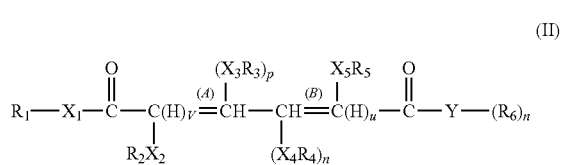

(II)

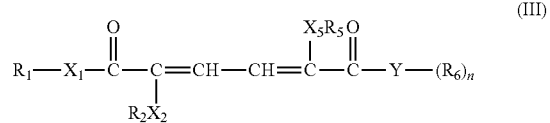

(III)

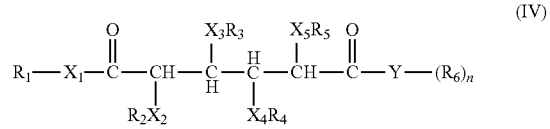

(IV)

-continued

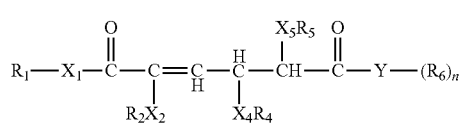 (V)

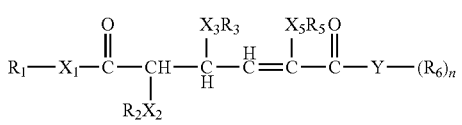 (VI)

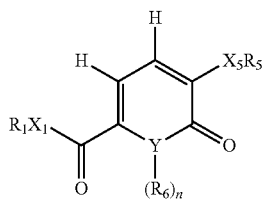 (VII)

in which $X_1$, $X_2$, $X_3$, $X_4$, $X_5$, $R_1$, $R_2$, $R_3$, $R_4$, $R_5$, Y, m, n, v, u, p and q if present are as defined above.

A preferred example of the compound of formula (I), when it is in linear form, is 2,5-dihydroxyhexa-2,4-diene-dioic acid, known as 2,5-dihydroxy muconic acid.

The structural formula of this muconic acid is as follows:

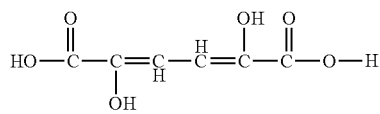 [SMILES: O=C(O)C(O)=CC=C(O)C(=O)O]

Preferably, muconic acid is a mixture of trans-trans, cis-trans, and cis-cis isomers.

Another preferred example of the compound of formula (I), when it is in the cyclic form, is a lactone, i.e. a cyclic compound in which the heteroatom in the ring is oxygen (Y=O), known as pyrone.

Preferably, the pyrone used is an alpha-pyrone.

Preferably, the alpha-pyrone is the ethyl ester of 5-hydroxy-6-oxo-6H-pyran-2-oic acid.

The structural formula of this alpha-pyrone is as follows:

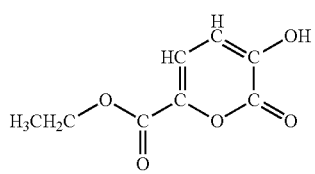

Some examples are given below of the compound of formula (I) that are preferred along with muconic acid and pyrone.

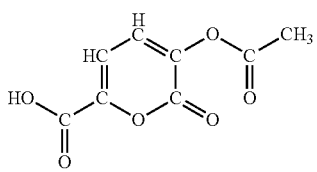

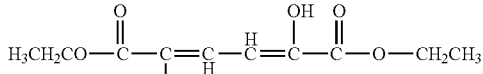
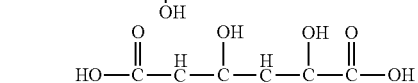
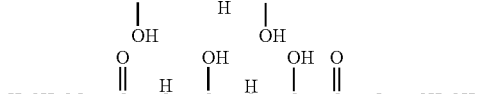
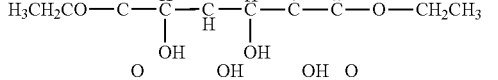

Said carbon allotrope may comprise, on the appropriate substrate, functional groups selected from the group consisting of:
- oxygenated functional groups, preferably hydroxyls, epoxides;
- functional groups containing carbonyls, preferably aldehydes, ketones, carboxylic acids;
- functional groups containing nitrogen atoms, preferably amines, amides, nitriles, diazonium salts, imines;
- functional groups containing sulfur atoms, preferably sulfides, disulfides, mercaptans, sulfones, sulfinic and sulfonic groups.

A wide range of carbon allotropes is thus available.

The carbon fillers according to the present invention are carbon allotropes in which the carbon is $sp^2$ hybridized. In particular, they may be: carbon black, graphene, graphite (for example graphite with a number of graphene sheets between 2 and 10000), single-wall or multi-walled carbon nanotubes, carbon nanotubes with longitudinal extension or helical, nanocones, nanohorns, nanotoroids, other nanotube or graphene structures (for example graphene clusters, graphene tapes, 2D or 3D networks of graphene or nanotubes, graphite crystals), fullerene.

According to the present description the terms "carbon allotrope" and "carbon filler" are used interchangeably, and/or are both indicated with the abbreviation CA.

The carbon allotropes, being more or less reactive aromatic systems, are subject to various types of intermolecular interaction. These include stacking. Stacking is defined as a stacked arrangement of aromatic molecules. Molecules containing aromatic rings in fact tend to become arranged spontaneously stacked on one another. Hence the concept of aromatic interaction (or π-π interaction), meaning a bond of the noncovalent type that is established between organic compounds containing aromatic groups, owing to intermolecular superposition of the p orbitals in the π-conjugated systems.

The carbon allotropes may also give rise to intermolecular interactions with formation of covalent bonds. These intermolecular interactions with formation of covalent bonds are typical of aromatic polycyclic systems. They are for example: 1,3-dipolar cycloadditions, Diels-Alder reaction.

According to the Applicants, in the compound of formula (I) there may be double bonds activated by the presence of electron-attracting atoms, such as oxygen atoms, which may give rise to interactions with the carbon allotropes with the formation both of noncovalent bonds and of covalent bonds.

According to the present description, the term "adduct" means a compound whose components are bound together more or less stably.

Without being restricted by any theory, in the reaction of formation of the adduct, the following two types of interaction may be presumed:

(i) π-π interaction. π-π interaction may exist between systems that possess π electrons, thus having $sp^2$ or sp hybridization. The interaction is between a doublet of π electrons and a σ orbital, or between the electrons of a σ orbital and a π orbital, or between the electrons of two π orbitals. This type of adduct is also known as "π complex". As stated above, this type of interaction leads to stacking.

(ii) covalent bonds between the compound of formula (I) and the carbon allotrope, by one of the reactions described above.

As stated above, the carbon allotropes may comprise functional groups of various kinds. In this context, an addition reaction may be carried out between a compound of formula (I) that contains functional groups of a polar nature and the carbon allotrope that comprises the functional groups. Formation of the adduct may also be carried out by interaction between the functional groups of the compound of formula (I) and the functional groups present on the carbon allotrope. These interactions may be of an intermolecular nature, such as hydrogen bonds and dipole interactions, or of a covalent nature, such as for example an esterification by reaction with an acid group. According to an important aspect of the invention, this interaction (both of an intermolecular nature and of a covalent nature) may even be effected just by supply of energy (for example mechanical energy, thermal energy, or irradiation with photons) and not with the use of solvents.

According to another aspect, the present invention relates to a process for preparing an adduct as described above, comprising the steps of forming a mixture of at least one compound of formula (I) and at least one $sp^2$ hybridized carbon allotrope, and supplying energy to said mixture to produce an interaction between functional groups of said compound and said allotrope.

For example, this process may comprise:
i. providing a solution of at least one compound of formula (I) in a polar protic or aprotic solvent selected from the group consisting of: water, alcohols, carbonyl solvents such as acetone, esters such as ethyl acetate, dimethylsulfoxide, acetonitrile, ethers;
ii. providing a suspension of the carbon allotrope in the polar protic or aprotic solvent used for preparing the solution as in point i.;
iii. mixing said solution and said suspension using systems for mechanical or magnetic stirring, or by sonication with sonication apparatus;
iv. removing said solvent from the mixture obtained in step iii.;

The process according to the present invention preferably further comprises:
v. supplying thermal energy and/or mechanical energy and/or energy by irradiation with photons to the mixture obtained.

Preferably the thermal energy is supplied at a temperature between 50 and 180° C. for a time between 15 and 360 minutes.

Preferably the mechanical energy is supplied for a time between 1 and 360 minutes.

Preferably the energy by irradiation with photons is supplied at a wavelength between 200 and 380 nm for a time between 30 and 180 minutes.

The procedure described in the preceding points results in obtaining a homogeneous relative dispersion of the carbon allotrope and of at least one compound of formula (I) and then obtaining homogeneous dispersion of the compound of formula (I) on the carbon filler. The solvents are removed before the successive actions aimed at transferring energy to the adduct between the carbon filler and the compound of formula (I).

The term "solvent" refers to the compound of formula (I) and not the carbon allotrope, for which it only acts as a dispersing means. The solvent is preferably an environmentally friendly solvent, for example water.

Generally, owing to the chemical nature of carbon, dispersion of carbon fillers in liquid matrices is rather difficult. The use of ultrasound makes it possible to disperse the carbon filler in a short time and improve the homogeneity of the dispersion (even just a few seconds). Moreover, the use of sonication makes it possible to separate, to a varying extent, the carbon fillers into the fundamental units. For example, carbon nanotubes may be separated into individual tubes from the tangle in which they are intertwined with other tubes. It is advisable to use low-power sonicators, for example ultrasonic baths. With suitable solvents (for example aromatic solvents, halogenated solvents, dimethylformamide, N-methyl pyrrolidone) it is also possible to bring about at least partial exfoliation of a graphite having a varying starting number of stacked layers and/or at least partial disentanglement of carbon nanotubes. Graphites with a small number of stacked layers have nanometric dimensions and are called nanographites. It is therefore preferable to contact the nanofiller first with a liquid so as to facilitate subsequently, by sonication and depending on the nanofiller, either the so-called disentanglement of the carbon nanotubes or exfoliation, more or less pronounced, of the graphite or nanographite. This procedure results in improvement of contact between the nanofiller and the compound of formula (I), also leading to an increase in exposed area of the nanofiller.

Irradiation with ultrasound gives rise, for a field intensity above a certain threshold value, to a cavitation effect in the solution. The gas microcavities (bubbles) present in the solution, subjected to successive expansion and contraction induced by the oscillating sound pressure field, get bigger and then implode, producing zones with extremely high temperature and pressure, which facilitate dispersion of the carbon allotrope in the solvent.

However, dispersion of the carbon allotrope in the solvent that also contains the compound of formula (I) may also take place solely by mechanical and/or magnetic stirring.

The procedure for removing the solvent from the mixture obtained may take place by any method suitable for removing solvent, for example vacuum evaporation, spray drying, etc.

The reaction of formation of the adduct is carried out with energy transfer to the system consisting of the compound of formula (I) and the carbon allotrope. Energy transfer is carried out for the purpose of improving the interaction between the compound of formula (I) and the carbon allotrope. In the absence of energy transfer, interaction between the compound of formula (I) and the carbon allotrope is weaker. Weaker interaction may lead to partial release of the compound of formula (I) from the carbon allotrope, especially if the adduct is in an environment of a polar nature.

As stated above, the forms of energy that may be transferred to the composition to contribute to formation of the adduct are:
- mechanical energy;
- thermal energy;
- photons.

Mechanical Energy

The mechanical treatment may consist for example of putting the powder obtained (allotrope/compound of formula (I)) in a ball mill, for example comprising a jar equipped with stainless steel spheres. Once closed, said jar is placed in a planetary mixer and is rotated at speeds from 200 to 500 rpm for times from 1 to 360 minutes. The powder is poured out immediately afterwards.

The mechanical treatment referred to is used either for promoting separation of the carbon allotropes into their fundamental components (for example exfoliation in the case of graphite), or for promoting relative dispersion of the allotrope and of the compound of formula (I), in order to obtain better distribution of the compound of formula (I) on the allotrope, or for inducing the development of more stable interaction.

Thermal Energy

The thermal treatment may consist for example of putting the powder obtained (carbon allotrope/compound of formula (I)) in a reaction flask, equipped with a condenser or in a closed flask. Once the reactor has been set up on a hot plate, the reaction is carried out at temperatures from 130 to 180° C. Heating is maintained for between 15 and 360 minutes.

Photons

The treatment with photons may consist for example of putting the powder obtained (carbon allotrope/compound of formula (I)) in a laboratory crystallizer forming a thin layer or putting the powder in a closed quartz flask. Once the reactor has been set up inside a dark chamber equipped with a low-pressure mercury lamp at 254 nm (or using a Rayonet® reactor equipped with the same type of lamp) the mixture is irradiated for variable times from 30 to 180 minutes. At the end of this time the mixture is transferred and analyzed.

By means of the present invention it is possible to obtain very stable suspensions or dispersions of adducts, either in aqueous media or in other substrates such as polymer compounds or rubbers, so as to obtain homogeneous products that have the particular characteristics of carbon nanofillers, such as for example high mechanical properties, high electrical conductivity, resistance to high temperatures, and flame-retardant properties.

Moreover, with an adduct according to the present invention it is possible to obtain uniform, continuous layers of black fillers (in the form of an adduct) on various substrates in order to obtain highly conductive surfaces.

In particular, a preferred aspect of the present invention is represented by an elastomer composition comprising the adducts between $sp^2$ hybridized carbon allotropes and compounds of formula (I) according to the present invention and as described above.

The elastomer compositions according to the present invention comprise at least one unsaturated elastomer selected from the group consisting of: poly(1,4-cis-isoprene), both natural rubber and synthetic polymer, poly(3,4-isoprene), poly(butadiene) (in particular poly(butadiene) with high content of 1,4-cis units), isoprene/isobutene copolymers, halogenated isoprene/isobutene copolymers such as for example halogenated butyl rubber, in particular chlorobutyl and bromobutyl rubber, 1,3-butadiene/acrylonitrile copolymers, styrene/1,3-butadiene copolymers, styrene/isoprene/1,3-butadiene copolymers, styrene/1,3-butadiene/acrylonitrile copolymers, or mixtures thereof.

The preferred elastomers for tire compounds are mainly poly(1,4-cis-isoprene) (from Hevea brasiliensis and synthetic), poly(1,4-butadiene) (BR rubber), poly(styrene-co-butadiene) (SBR rubber) or mixtures thereof. All these polymers are nonpolar hydrocarbons.

The elastomer compositions according to the present invention may, moreover, contain at least one elastomer of one or more mono-olefins. The mono-olefins may be selected from: ethylene and 1-olefins that contain from 3 to 12 carbon atoms, such as, for example, propylene, 1-butene, 1-pentene, 1-hexene, 1-octene, or mixtures of these mono-olefins.

The elastomer of one or more mono-olefins may contain a diene, which generally contains from 4 to 20 carbon atoms and is preferably selected from: 1,3-butadiene, isoprene, 1,4-hexadiene, 1,4-cyclohexadiene, 5-ethylidene-2-norbornene, 5-methylene-2-norbornene, vinyl norbornene or mixtures of these dienes. The diene may optionally be halogenated.

Among these elastomers of one or more mono-olefins, the following are preferred: ethylene/propylene copolymers (EPR) or ethylene/propylene/diene copolymers (EPDM), poly(isobutene).

The elastomer compositions may in addition contain an elastomer, unsaturated, diene or based on non-diene monomers, functionalized for reaction with a suitable terminating agent or coupling agents. In particular, the diene elastomeric polymer may be obtained by anionic polymerization promoted by an organometallic initiator (in particular an alkyllithium) and terminated by reaction with suitable terminating agents or coupling agents such as, for example, epoxides, carbonyl compounds such as for example cyclohexanone and benzophenone, substituted or unsubstituted, imines, carbodiimides, alkyl-tin halides, alkoxysilanes or aryloxysilanes.

According to a preferred embodiment, said elastomer composition additionally comprises further reinforcing fillers selected from the group comprising: carbon black, silica, layered silicates, mixed oxides of aluminum and magnesium with lamellar structures, alumina, aluminosilicates.

The elastomer composition may be prepared by mixing together the polymer components with the adducts between $sp^2$ hybridized carbon allotropes and compounds of formula (I) according to the present invention, and with the other reinforcing fillers and the other additives optionally present, according to the techniques known in this sector. Mixing may be carried out, for example, using an open mixer of the "open-mill" type and/or an internal mixer of the type with tangential rotors (Banbury®), and/or with intermeshing rotors (Intermix™), and/or in continuous mixers of the Ko-Kneader™ type, and/or of the twin-screw or multi-screw type, and/or of the planetary type.

Some examples of preparation of the adduct comprising a compound of formula (I) and a carbon allotrope according to the present invention will be described below.

These examples will also be illustrated with reference to the appended drawings; in which.

Figure 9A:
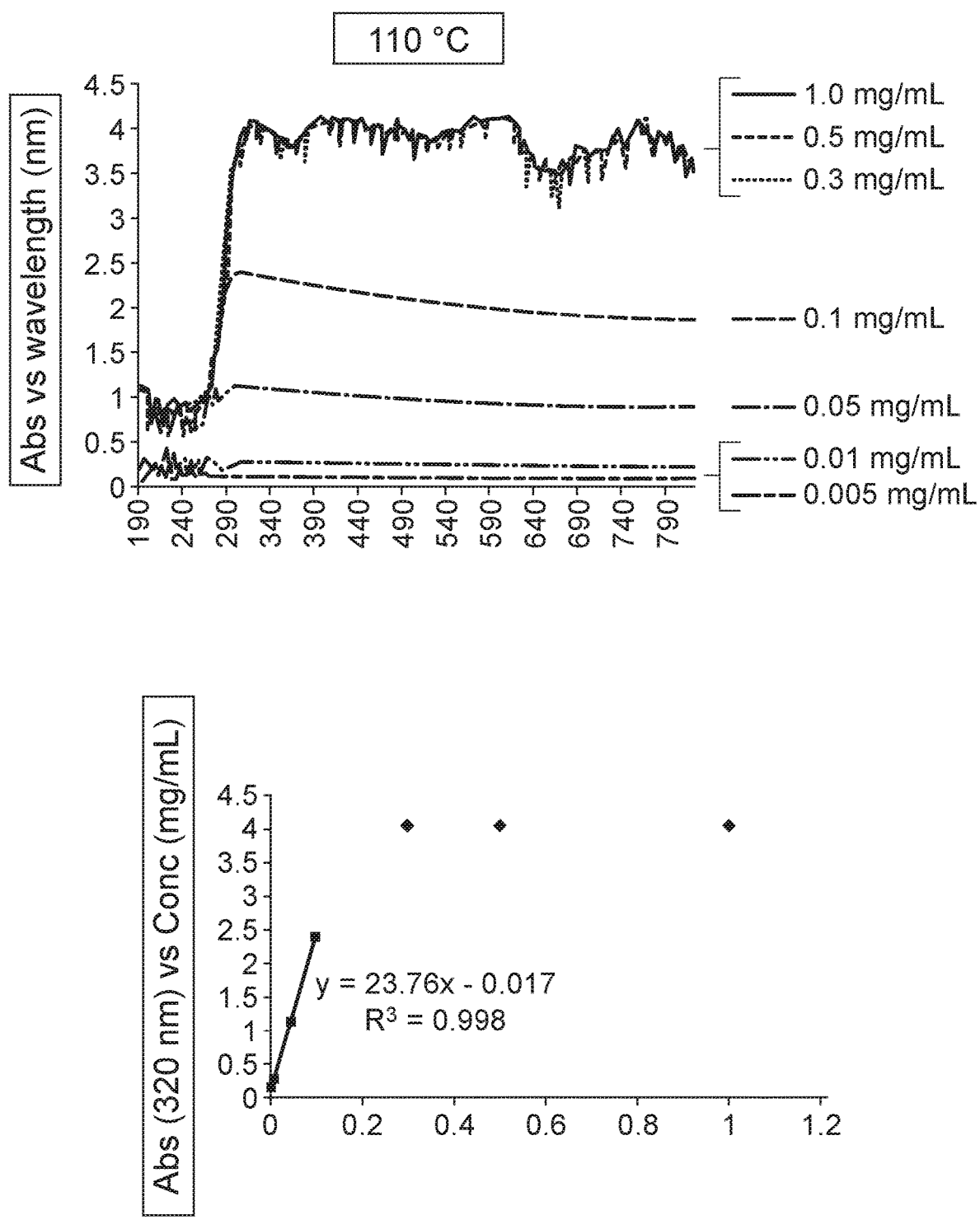
Figure 9B:
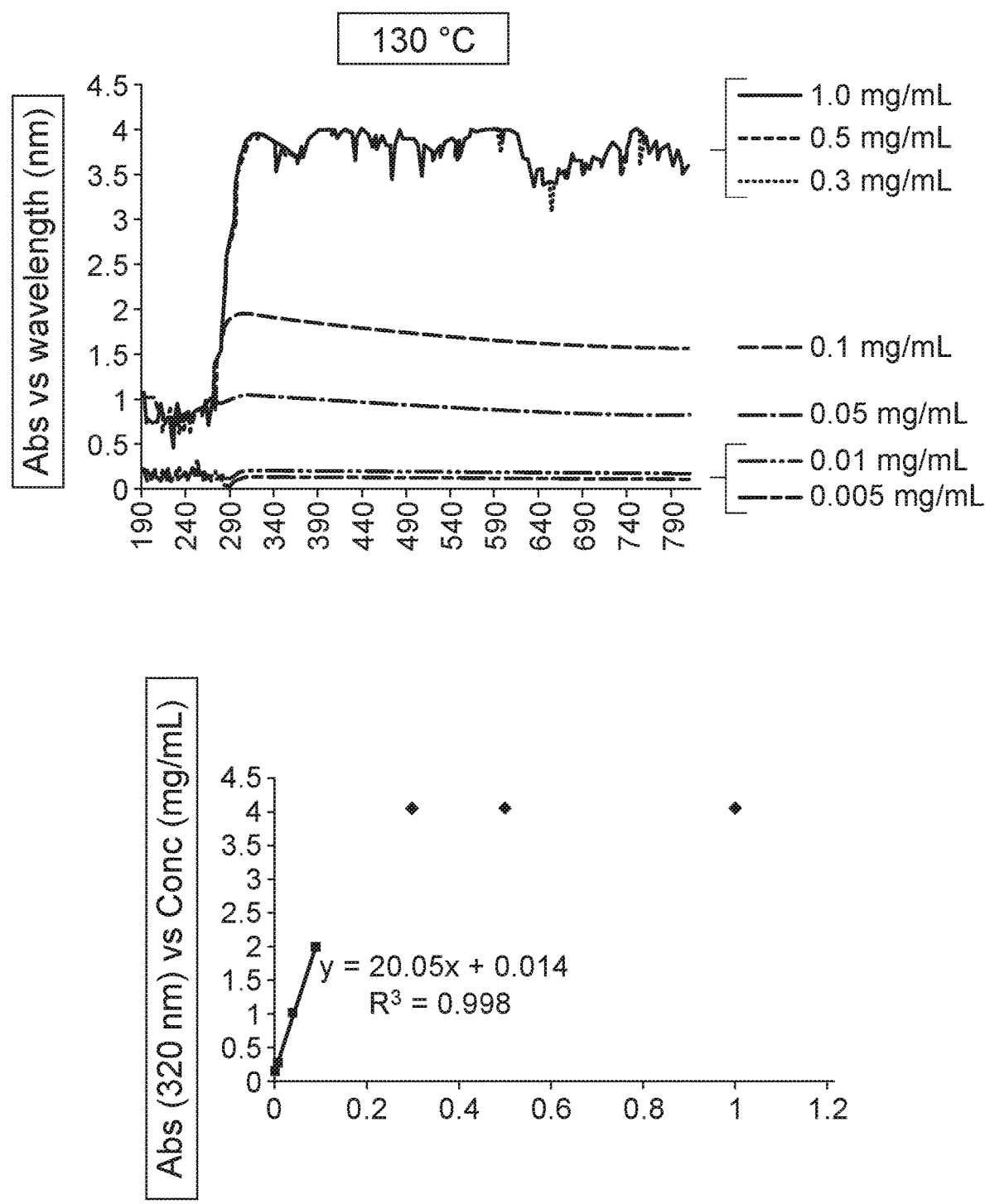
Figure 9C:
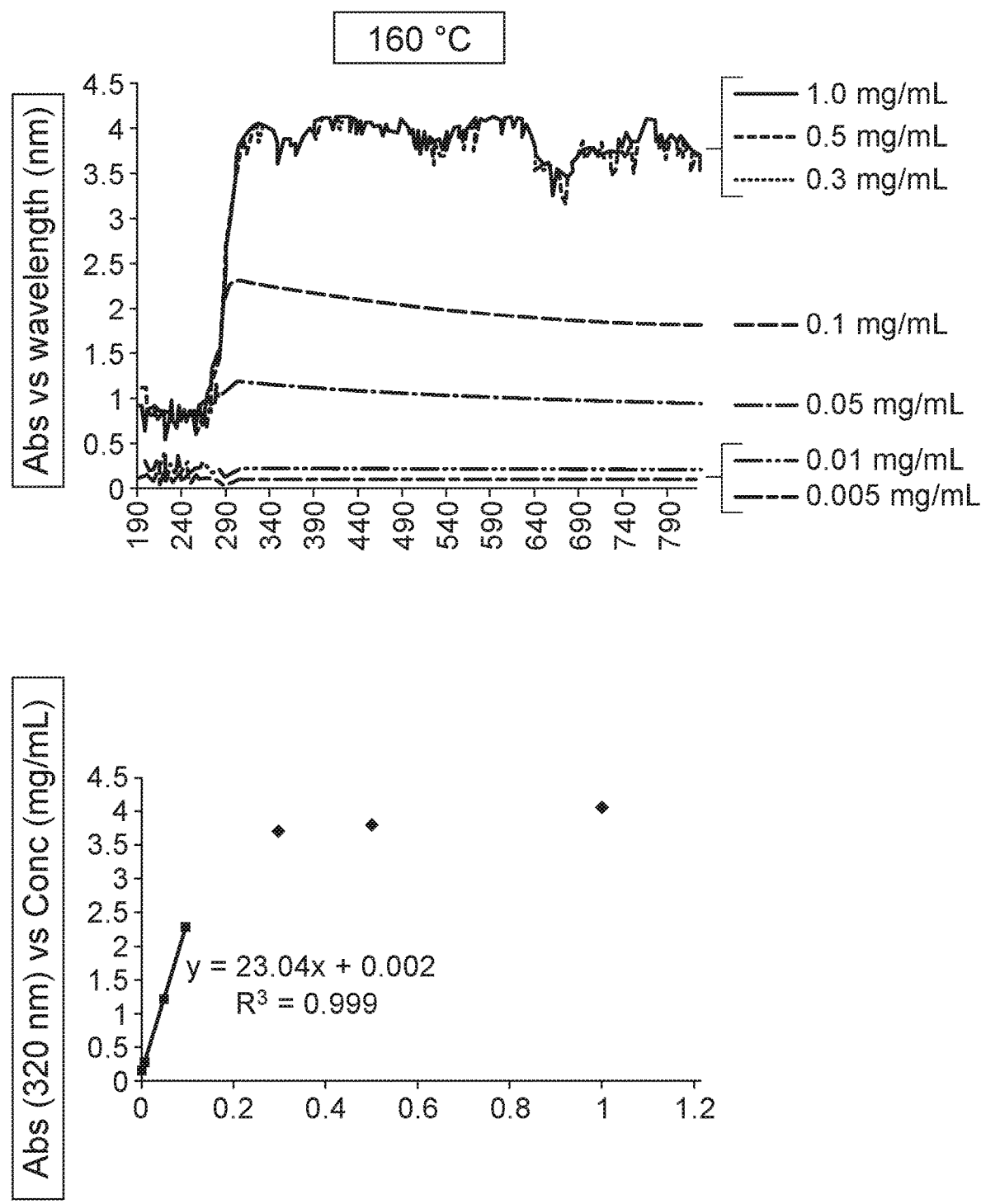
Figure 10A:
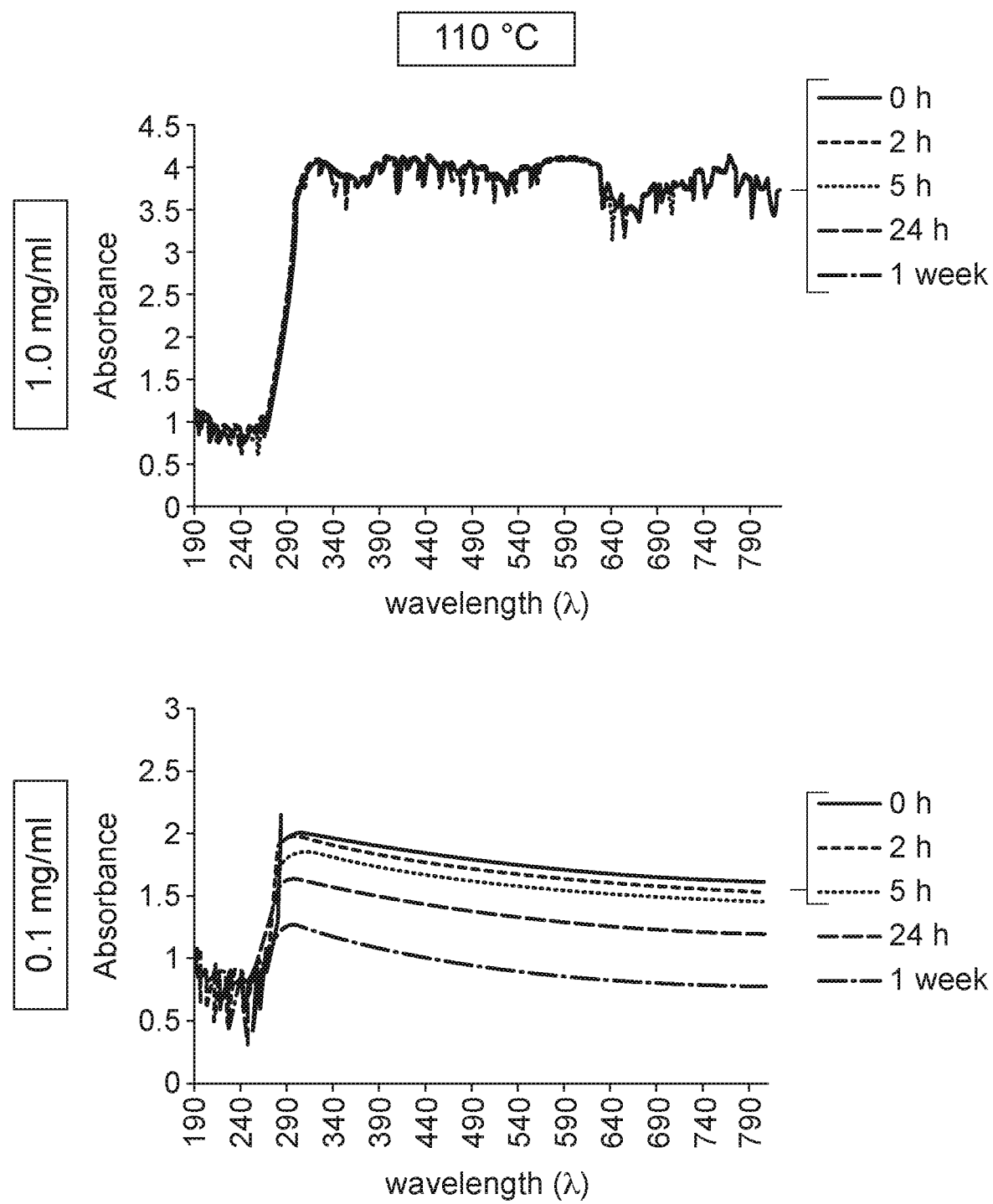
Figure 10B:
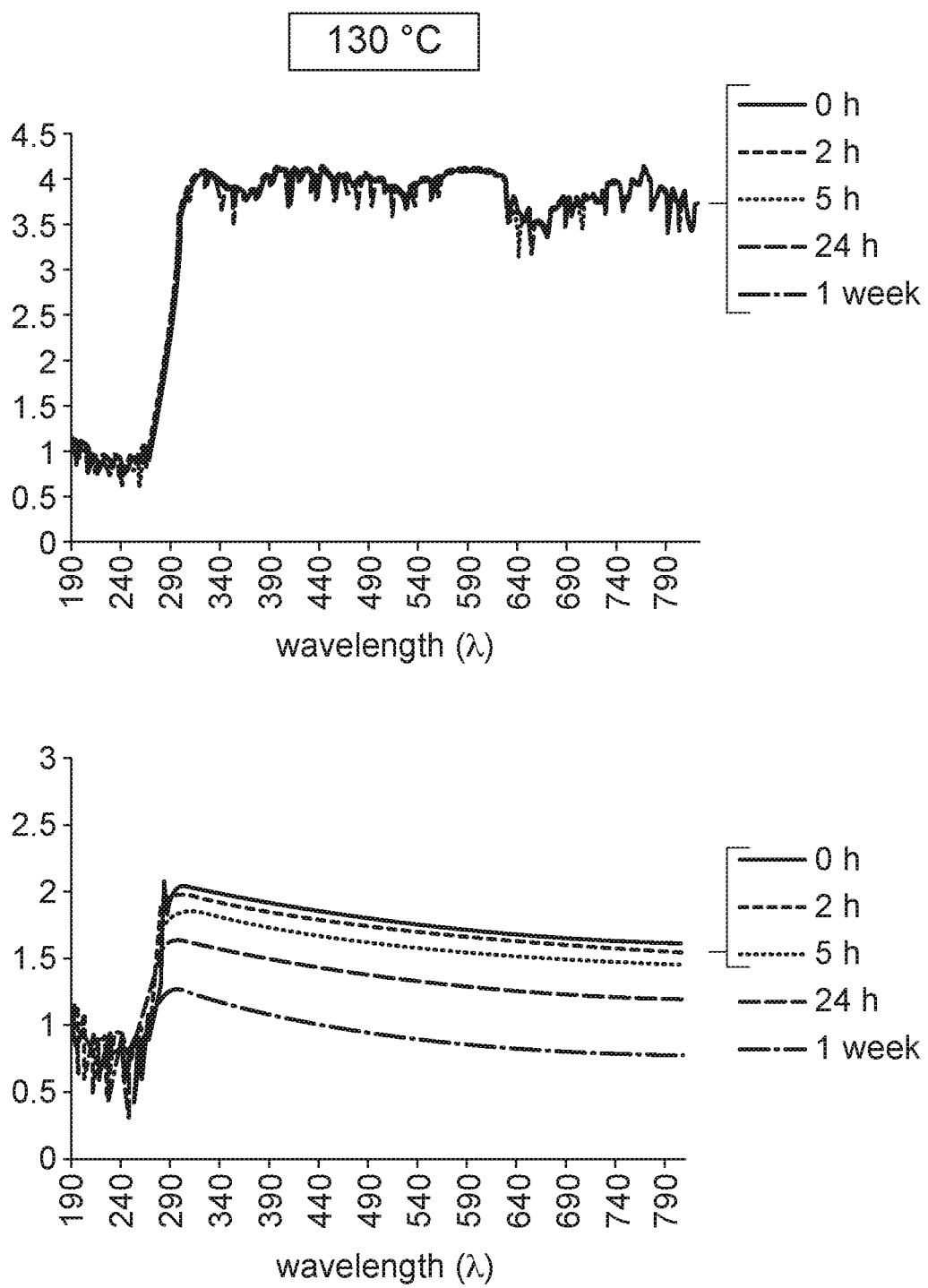
Figure 10C:
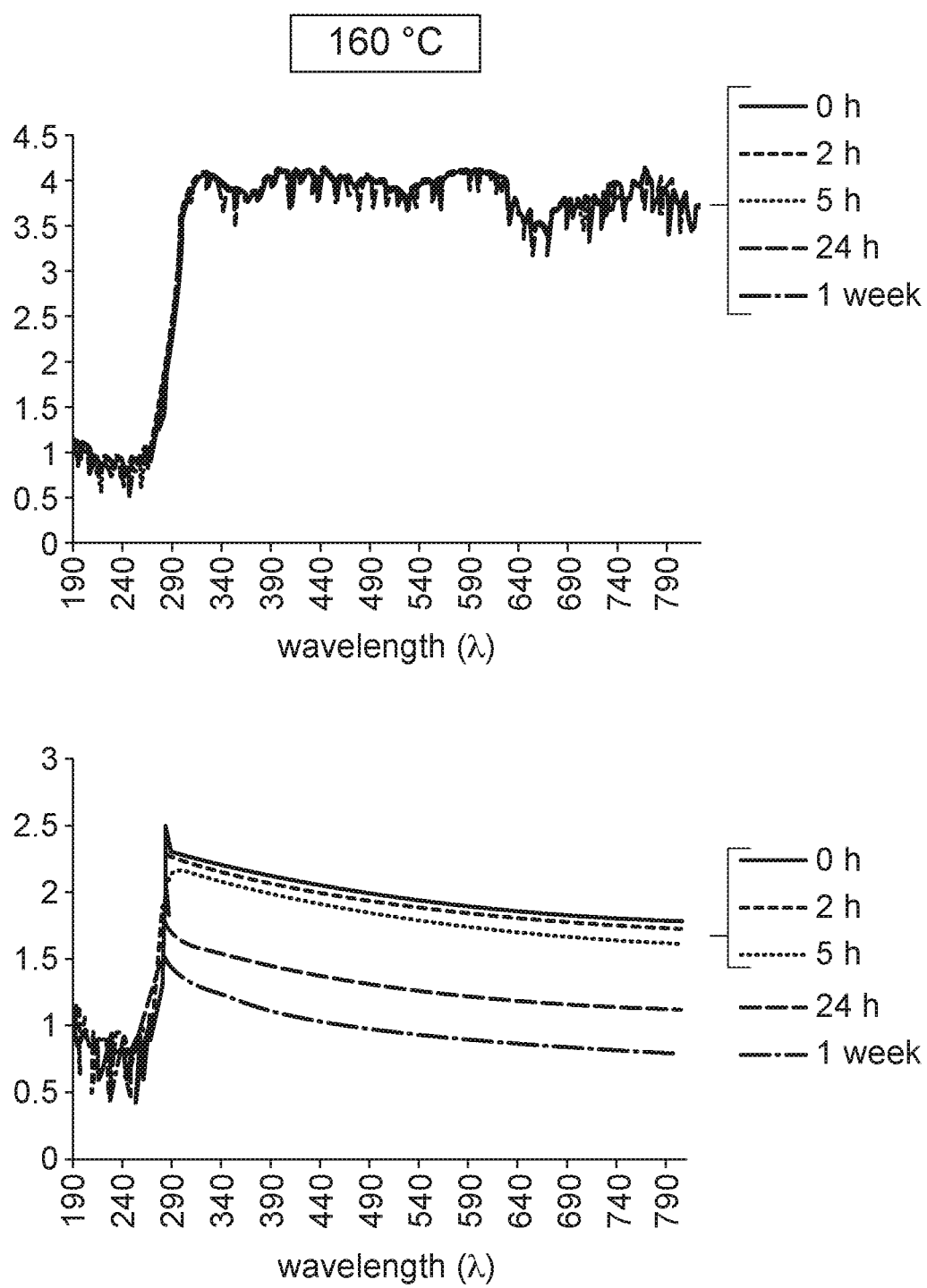
Figure 11:

FIGS. 9a-c show the UV-VIS MEASUREMENTS of suspensions of adducts according to the invention;

FIGS. 10a-c show the UV-VIS MEASUREMENTS the stability over time of suspensions of adducts according to the invention;

FIG. 11 shows the UV-VIS MEASUREMENTS of the absorbance-wavelength relation of adducts according to the invention.

EXAMPLES

All the chemicals used in the syntheses given in the following examples were purchased from: mucic acid (Aldrich), acetic anhydride (Aldrich), acetone (Aldrich), sodium acetate trihydrate (Carlo Erba reagenti). It should be pointed out that mucic acid is derived from a monosaccharide, galactose, which is of natural origin.

The multi-walled carbon nanotubes (MWCNT or CNT) (NC7000 series) were purchased from NANOCYL™ Inc (www.nanocyl.com) and used as supplied by the seller.

The graphites used in the present invention were purchased from Asbury Graphite Mills Inc. The following commercial grades were used: Synthetic Graphite 8427® (HSAG), NG24, NG27, NG307, G3806, SFG6,G3807. The carbon black (CB) used in the present invention was acquired from Cabot. The following commercial grades were selected: CB N326, CB N234, CB N115(CB).

The adducts obtained in the examples presented hereunder were analyzed as follows:

$^1$H-NMR and $^{13}$C-NMR the $^1$H-NMR and $^{13}$C-NMR spectra were recorded with a Bruker 400 MHz instrument (100 MHz $^{13}$C) operating at 298 K. The chemical shifts are given in parts per million (ppm) with the peaks of the solvent residues as internal standard (DMSO-d6: $\delta_H$=2.50 ppm, CDCl$_3$: $\delta_H$=7.26 ppm).

X-Rays (Powder X-Ray Diffraction)

the X-ray profiles (Wide-angle X-ray diffraction (WAXD)) were obtained in rereflection, using a diffractometer "automatic Bruker D8 Advance diffractometer, with nickel filtered Cu—Kα radiation"). The profiles were recorded in the range of 2θ between 10° and 100°.

Thermogravimetric Analysis (TGA)

Thermogravimetric analysis (TGA tests) under a stream of N$_2$ (60 mL/min) was carried out using a Mettler TGA SDTA/851 instrument according to standard method ISO9924-1. The samples (10 mg) were heated from 30 to 300° C. at 10° C./min, holding at 300° C. for 10 min, and immediately thereafter heating to 550° C. (20° C./min). After holding them at 550° C. for 15 min, they are heated further to 650° C. at a rate of 30° C./min and held at 650° C. for 20 min under an air stream (60 mL/min).

FT-IR

The IR spectra were recorded in transmission (128 scans and 4 cm$^{-1}$ resolution) on diamond crystal (diamond anvil cell (DAC)) using a ThermoElectron FT-IR Continupm IR microscope.

The HRTEM images were obtained using a "Philips CM 200 field emission gun microscope" operating with a voltage of 200 kV. A few drops of the suspension were deposited on a grid (carbon-coated copper grid) of 200 mesh and dried for several hours prior to analysis. During acquisition of the HRTEM images, the sample did not undergo structural changes.

For measurement of UV-visible absorption, suspensions of the adducts (2 mL) were taken by Pasteur pipette and transferred to 1-cm quartz cuvettes (volume 1 or 3 mL) and analyzed using a Hewlett Packard 8452A Diode Array Spectrophotometer. The blank of the solvent used was recorded.

Determination of the Functionalization Yield

"Functionalization yield" means the quantity in wt % of molecule bound to the carbon allotrope with sp$^2$ hybridization. The functionalization yield of the adducts obtained according to the examples given in this description was calculated using the following equation, in which, as stated above, CA denotes carbon allotrope or carbon-containing substance:

Functionalization yield (%) =

$$100 * \frac{\substack{\text{Compound of formula } (I) \text{ by weight in} \\ (CA - \text{Compound of formula } (I) \text{ adduct}) \text{ after purification}}}{\substack{\text{Compound of formula } (I) \text{ by weight in} \\ (CA - \text{Compound of formula } (I) \text{ adduct}) \text{ before purification}}}$$

The values given for the purposes of the calculation of the yield refer to the quantity of the compound of formula (I) found by TGA before and after the purification step and refer to the losses (in wt %) found from the TGA plot in the temperature range from 0 to 700° C.

Hereinafter in the present description, the term "yield" means the functionalization yield, unless stated otherwise.

Examples 1-3. Synthesis of the Precursor of Pyrone and of Pyrones Example 1. Synthesis of 3,4,5-triacetoxy-6-oxo-tetrahydro-pyran-2-carboxylic acid (1) (Precursor)

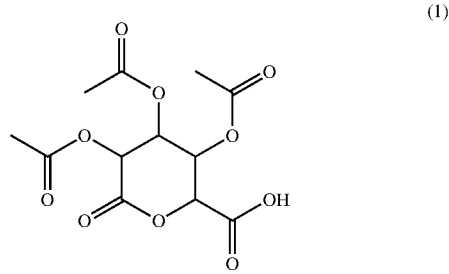 [SMILES: CC(=O)OC1C(=O)OC(C(=O)O)C(OC(C)=O)C1OC(C)=O]

(1)

A 100-mL flask equipped with a magnetic stirrer and a condenser is charged with 10 g of mucic acid (0.049 mol) and 51 mL of acetic anhydride (0.54 mol). The mixture was stirred at 130° C. overnight. The pure product was isolated by filtration.

The product was characterized by NMR spectroscopy: $^1$H NMR (400 MHz, DMSO-d6, δ in ppm): 2.08 (s, 3H); 2.15 (s, 6H); 5.01 (dd, 1H); 5.27 (d, 1H); 5.51 (t, 1H); 5.89 (d, 1H); 12.10 (s, 1H) as shown in FIG. 1.

Figure 1:
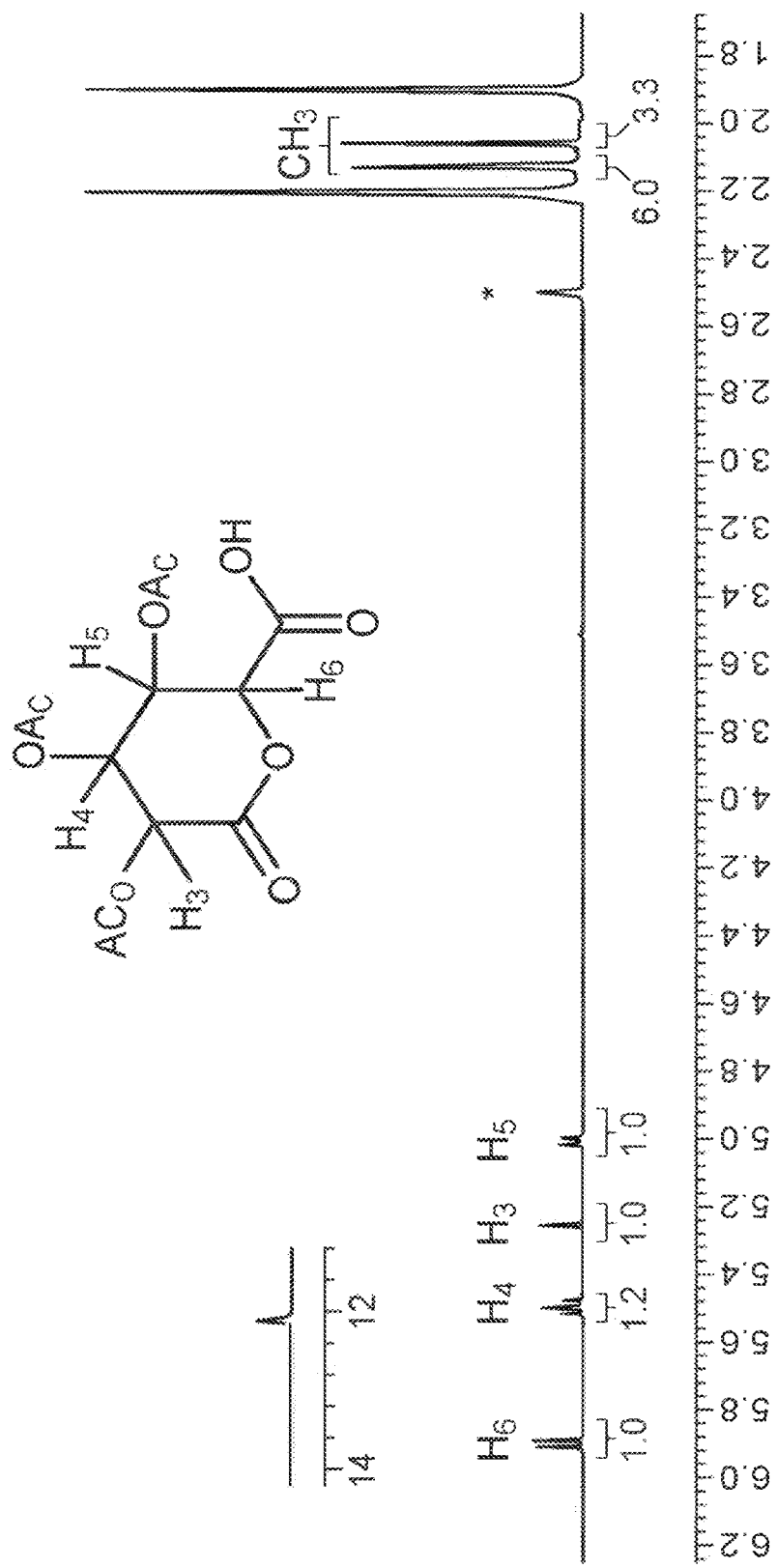
FIG. 1 shows the $^1$H-NMR spectrum [400 MHz in DMSO-$d_6$ (*)] of 3,4,5-triacetoxy-6-oxo-tetrahydro-pyran-2-carboxylic acid (1)

In particular, in the spectrum of the reaction mixture given in FIG. 1, attention should be paid to the signals due to 3,4,5-triacetoxy-6-oxo-tetrahydro-pyran-2-carboxylic acid (1), at excess of acetic anhydride and acetic acid. The $^1$H NMR spectrum, with the relevant attributions, confirms the structural formula shown in the figure.

The synthesis yield is 99% with an atom economy (AE) of 77% and a reaction mass efficiency (RME) of 76%.

Example 2. Synthesis of 5-acetoxy-6-oxo-6H-pyran-2-carboxylic acid

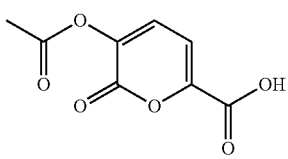

(2)

A 100-mL flask equipped with a magnetic stirrer and a condenser is charged with 1 g of $CH_3COONa \cdot 3H_2O$ (0.049 mol) and the reaction mixture obtained in example 1. The new reaction mixture is then stirred for 12 hours at 100° C. At the end of this time, HCl solution (0.0002 mol; 2 ml; 36%) is added and a few minutes after addition it is noted that there is formation of a white precipitate (59.8 g). Once formed, the precipitate is removed by filtration. The solution, on the other hand, is concentrated at reduced pressure until about 32 g of solution is obtained. The solution thus obtained is left to stand until a new precipitate has formed. After 1 day, the procedure is repeated and a further 3.2 g of solid is isolated. The solid product of the 3 filtrations was characterized by NMR spectroscopy.

Figure 2:
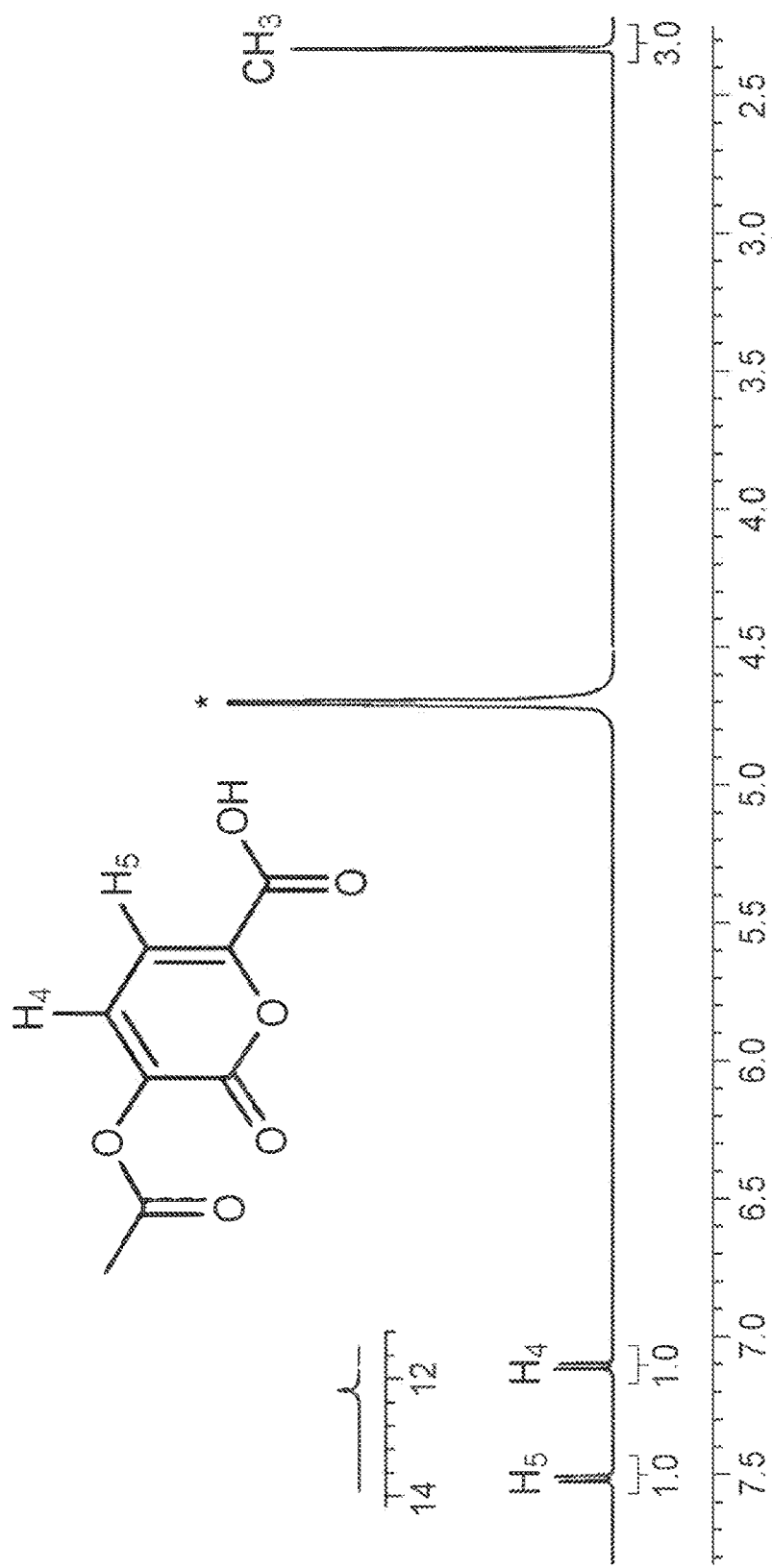
FIG. 2 shows the $^1$H-NMR spectrum [400 MHz in D$_2$O (*)] of 5-acetoxy-6-oxo-6H-pyran-2-carboxylic acid (2)

The product was characterized by $^1$H NMR spectroscopy (400 MHz, DMSO-d6, δ in ppm): 2.27 (s, 3H); 7.13 (d, 1H); 7.47 (d, 1H); 12.10 (s, 1H) as shown in FIG. 2.

In particular, in the spectrum of the reaction mixture given in FIG. 2, attention should be paid to the signals due to 5-acetoxy-6-oxo-6H-pyran-2-carboxylic acid (2): the doublets due to the hydrogens H4 and H5 are at 7.13 and 7.47 ppm and are in line with the chemical structure given in FIG. 2. The $^1$H NMR spectrum, with the relevant attributions, confirms the structural formula shown in the figure.

The synthesis yield is 65% with an atom economy (AE) of 62% and a reaction mass efficiency (RME) of 41%.

Example 3. Synthesis of the ethyl ester of 5-hydroxy-6-oxo-6H-pyran-2-carboxylic acid (3)

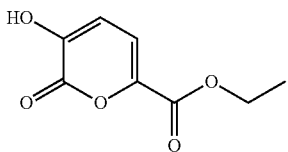

(3)

A 100-mL flask equipped with a magnetic stirrer and a condenser is charged with the product obtained in example 2 (2) (3.1 g), ethanol (30 ml) and six drops of sulfuric acid (1.0 g; 0.049 mol). The mixture thus obtained is stirred at 85° C. overnight. At the end of this time, the reaction mixture is poured into a separatory funnel and water is added (180 ml) and a small amount of sodium bicarbonate so as to bring the pH to neutral. The mixture is extracted 3 times with dichloromethane (60 ml). The residual water is basified with sodium bicarbonate. The organic phases are dried over sodium sulfate and then filtered and dried thoroughly at reduced pressure.

The product was characterized by $^1$H NMR spectroscopy (400 MHz, CDCl$_3$-d6, δ in ppm): 1.40 (t, 3H); 4.40 (q, 2H); 6.78 (d, 1H); 7.20 (d, 1H); $^{13}$C NMR (100 MHz, CDCl$_3$): δ 14.17, 62.17, 112.93, 113.00, 140.85, 145.70, 159.14, 159.59 ppm) as shown in FIG. 3.

Figure 3:
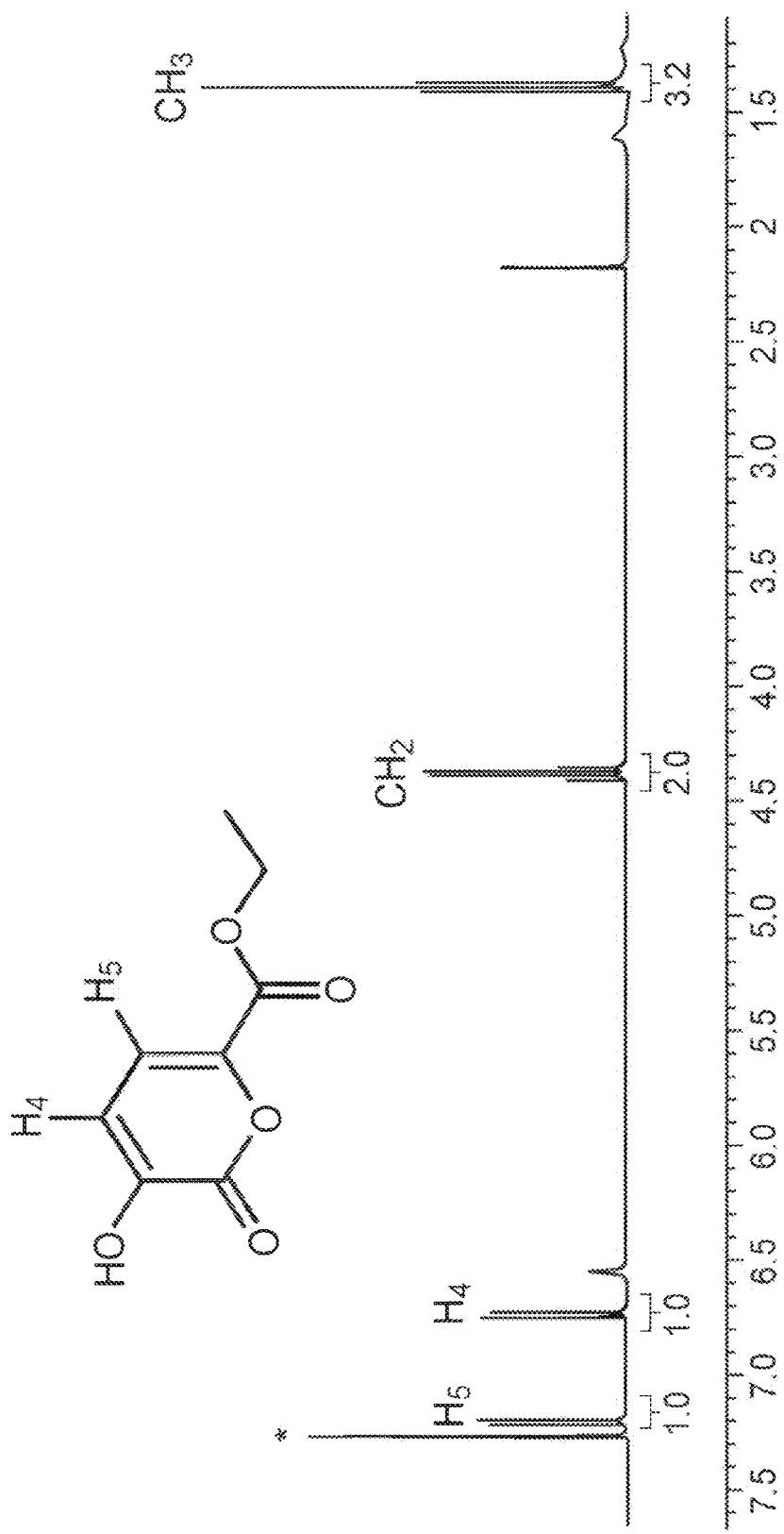
FIG. 3 shows the $^1$H-NMR spectrum [400 MHz in CDCl$_3$ (*)] of the ethyl ester of 5-hydroxy-6-oxo-6H-pyran-2-carboxylic acid (3)

The signals due to the ethyl ester of 5-hydroxy-6-oxo-6H-pyran-2-carboxylic acid (3) are clearly present in the spectrum in FIG. 3 and are in line with the chemical structure shown. The $^1$H NMR spectrum, with the relevant attributions, confirms the structural formula shown in the figure.

The synthesis yield is 99% with an atom economy (AE) of 63% and a reaction mass efficiency (RME) of 41%.

Examples 4-12. Preparation of Adducts of a Pyrone with High Surface Area Graphite (HSAG)

Example 4. Preparation of a Physical Mixture Between the Product of Example 2 and High Surface Area Graphite (HSAG)

In this example and in some subsequent examples, the mmols of graphite are indicated, which are calculated as the theoretical mmols of benzene rings without hydrogen. Where, in the subsequent examples, the mmols of carbon allotropes are given, they have been calculated in the same way.

High surface area graphite (HSAG) (100 mg, 72 mmol), compound 2 (100 mg, 1.3 mmol) and acetone (10 ml) are poured successively into a 50-mL single-neck flask. The mixture obtained is unstable and is therefore sonicated for 15 minutes using a 2 L ultrasonic bath. After this time the solvent is removed at reduced pressure. 200 mg of HSAG/2 physical mixture was obtained.

Example 5. Preparation of an Adduct Between the Product of Example 2 and High Surface Area Graphite (HSAG)

The physical mixture obtained in example 4 (50 mg) was poured into a flask and was heated at 130° C. for 2 hours. The powder thus obtained was analyzed. 45 mg of HSAG/2-T adduct was obtained.

Example 6. Preparation of an Adduct Between the Product of Example 2 and High Surface Area Graphite (HSAG)

The physical mixture obtained in example 4 (50 mg) was poured into a flask and was heated at 160° C. for 2 hours. The powder thus obtained was analyzed. 40 mg of HSAG/2-T adduct was obtained.

Example 7. Preparation of a Physical Mixture Between the Product of Example 3 and High Surface Area Graphite (HSAG)

High surface area graphite HSAG (1.8 g, 26.2 mmol), the product of example 3 (0.48 g, 2.62 mmol) and acetone (10 ml) are poured successively into a 100-mL single-neck flask.

The mixture obtained is unstable and is therefore sonicated for 30 minutes using a 2 L ultrasonic bath. After this time the solvent is removed at reduced pressure. 2.2 g of HSAG/3 physical mixture was obtained.

Example 8. Preparation of an Adduct Between the Product of Example 3 and High Surface Area Graphite (HSAG)

The physical mixture obtained in example 7 (400 mg) was poured into a flask and was heated at 110° C. for 8 hours. The black powder thus obtained was filtered on a Buchner and was washed with acetone (30 mL×3). The final yield is equal to 81%.

Example 9. Preparation of an Adduct Between the Product of Example 3 and High Surface Area Graphite (HSAG)

The physical mixture obtained in example 7 (400 mg) was poured into a flask and heated at 130° C. for 8 hours. The black powder thus obtained was filtered on a Buchner and was washed with acetone (30 mL×3). The final yield is equal to 83.4%.

Example 10. Preparation of an Adduct Between the Product of Example 3 and High Surface Area Graphite (HSAG)

The physical mixture obtained in example 7 (400 mg) was poured into a flask and heated at 150° C. for 8 hours. The black powder thus obtained was filtered on a Buchner and was washed with acetone (30 mL×3). The final yield is equal to 81.5%.

Example 11. Preparation of an Adduct Between the Product of Example 3 and High Surface Area Graphite (HSAG)

The physical mixture obtained in example 7 (400 mg) was poured into a flask and heated at 160° C. for 8 hours. The black powder thus obtained was filtered on a Buchner and was washed with acetone (30 mL×3). The final yield is equal to 91%.

Figure 4:
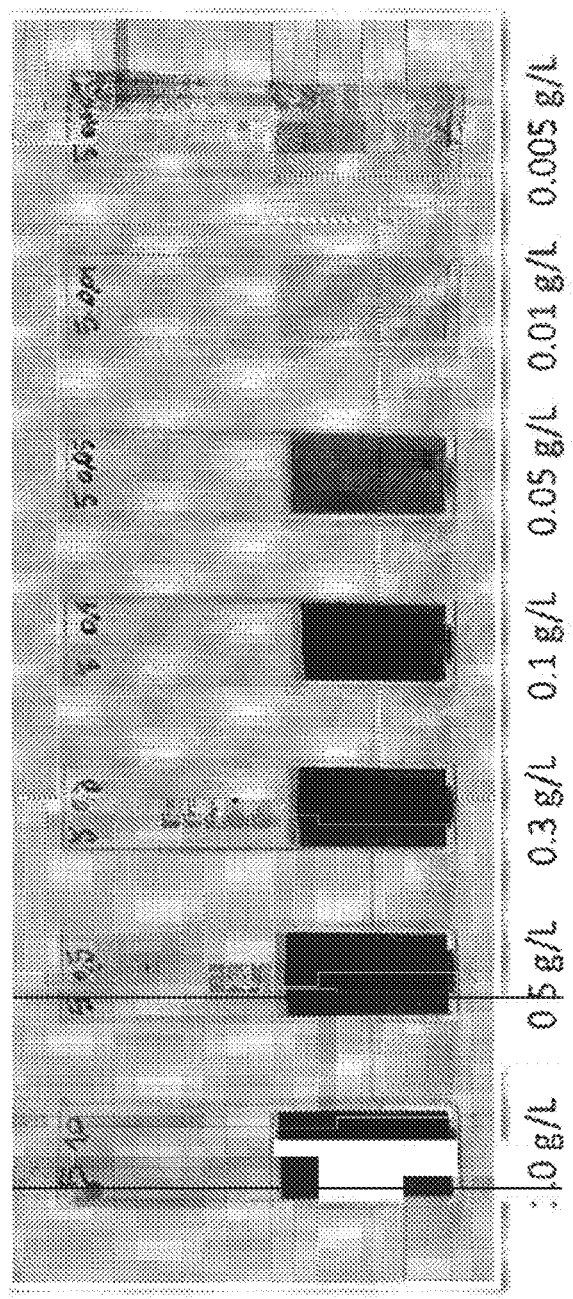
FIG. 4 shows the aqueous suspensions of adducts according to the invention.

FIG. 4 shows aqueous suspensions of the adduct of example 11 at various concentrations (1 mg/mL, 0.5 mg/mL, 0.3 mg/mL, 0.1 mg/mL, 0.05 mg/mL, 0.01 mg/mL, 0.005 mg/mL). The increase in concentration of the dispersions, passing from 0.005 mg/mL to 1 mg/mL, is observed qualitatively in FIG. 4.

Example 12. Preparation of an Adduct Between the Product of Example 3 and High Surface Area Graphite (HSAG)

The physical mixture obtained in example 7 (1 g) was poured into a jar in a Retsch S100 planetary ball mill, with the grinding jar moving in a horizontal plane, with a volume of 0.3 L. The jar was rotated at 300 rpm for 8 hours at room temperature. The black powder thus obtained was filtered on a Buchner and was washed with acetone (30 mL×3). The final yield is equal to 85.2%.

Examples 13-14. Preparation of Adducts of a Pyrone with Carbon Nanotubes (CNTs)

Example 13. Preparation of a Physical Mixture between the Product of Example 3 and Carbon Nanotubes (CNTs)

CNTs (1.8 g, 26.2 mmol), the product of example 3 (0.48 g, 2.62 mmol) and acetone (10 ml) are poured successively into a 100-mL single-neck flask. The mixture obtained is unstable and is therefore sonicated for 30 minutes using a 2 L ultrasonic bath. After this time the solvent is removed at reduced pressure. 2.0 g of CNT/3 physical mixture was obtained.

Example 14. Preparation of an Adduct Between the Product of of Example 3 and Carbon Nanotubes (CNTs)

The physical mixture obtained in example 13 (0.4 g) was poured into a flask and heated at 160° C. for 8 hours. The black powder thus obtained was filtered on a Buchner and was washed with acetone (30 mL×3). The final yield is equal to 96%.

Figure 5:
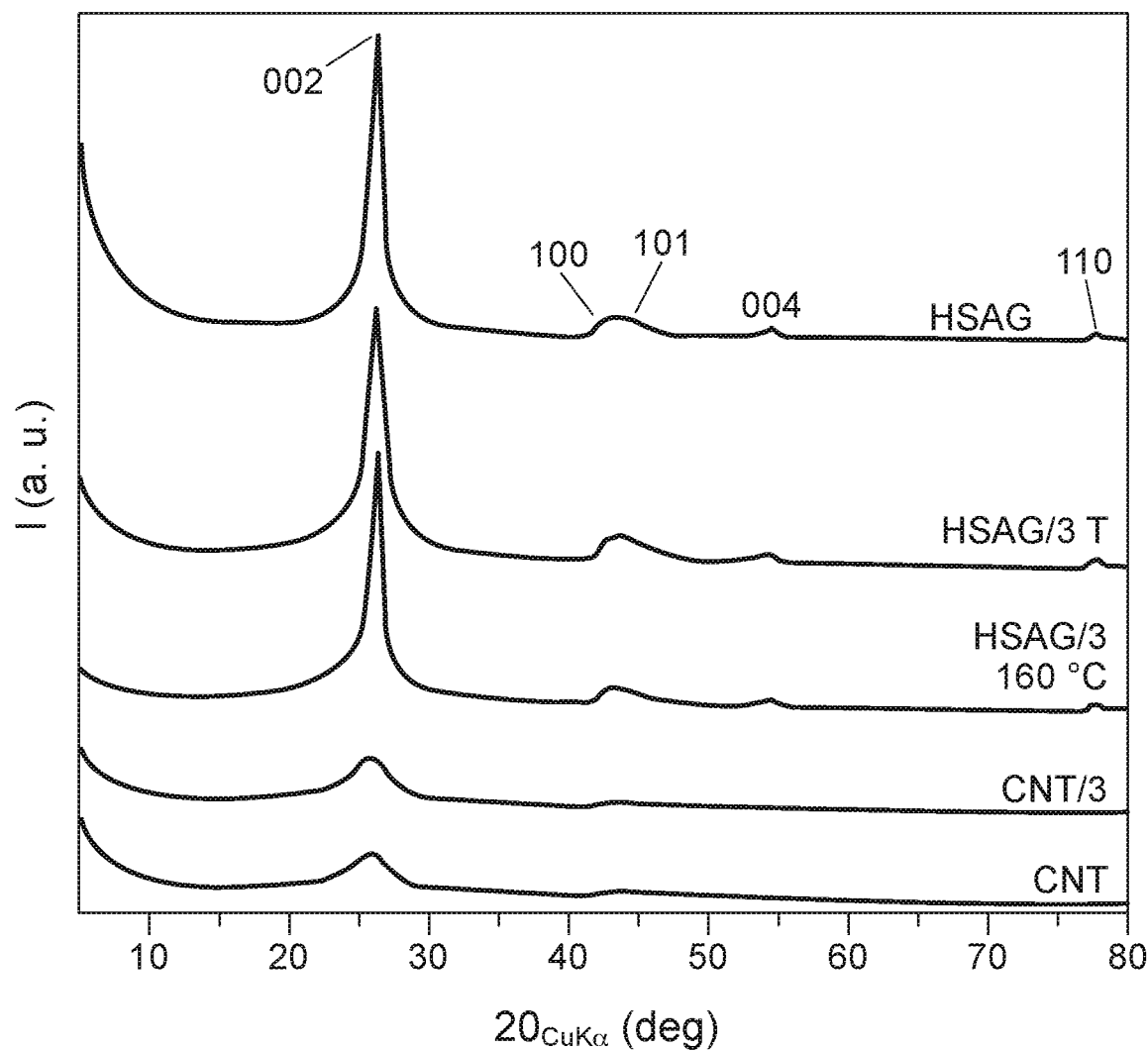
FIG. 5 shows the X-ray profiles (WAXD patterns) of HSAG, CNT, of adducts according to the invention.

FIG. 5 shows the X-ray profiles (WAXD patterns) of HSAG, CNTs and the adducts from examples 11, 12 and 14. The X-ray profiles of graphite (HSAG) and carbon nanotubes (CNTs) both show the presence of the (00$\ell$) reflection: 002 at 26.6° (2θ) relating to the crystalline order in the direction orthogonal to the stacked layers. In both profiles it is possible to assign the reflections to 100 and 110, at 42.5° and 77.6° (2θ), respectively. The number of stacked layers was estimated by applying the Scherrer equation to the 002 rereflection at about 35 for HSAG and 12 for the CNTs. With regard to the samples of graphite and carbon nanotubes functionalized with pyrone 3, it was found that in all cases the reflections already assigned for the starting allotropes, were found at the same values of 2θ, indicating that formation of the adducts did not promote expansion of the distance between the layers. The number of stacked layers in the adducts of HSAG and CNT with compound 3 was calculated by applying the Scherrer equation to the 002 reflection. From the calculation, the HSAG/3 and HSAG/3 T samples show 21 and 31 superposed layers, respectively. The adduct CNT/3 shows 10 stacked crystal layers.

Figure 6:
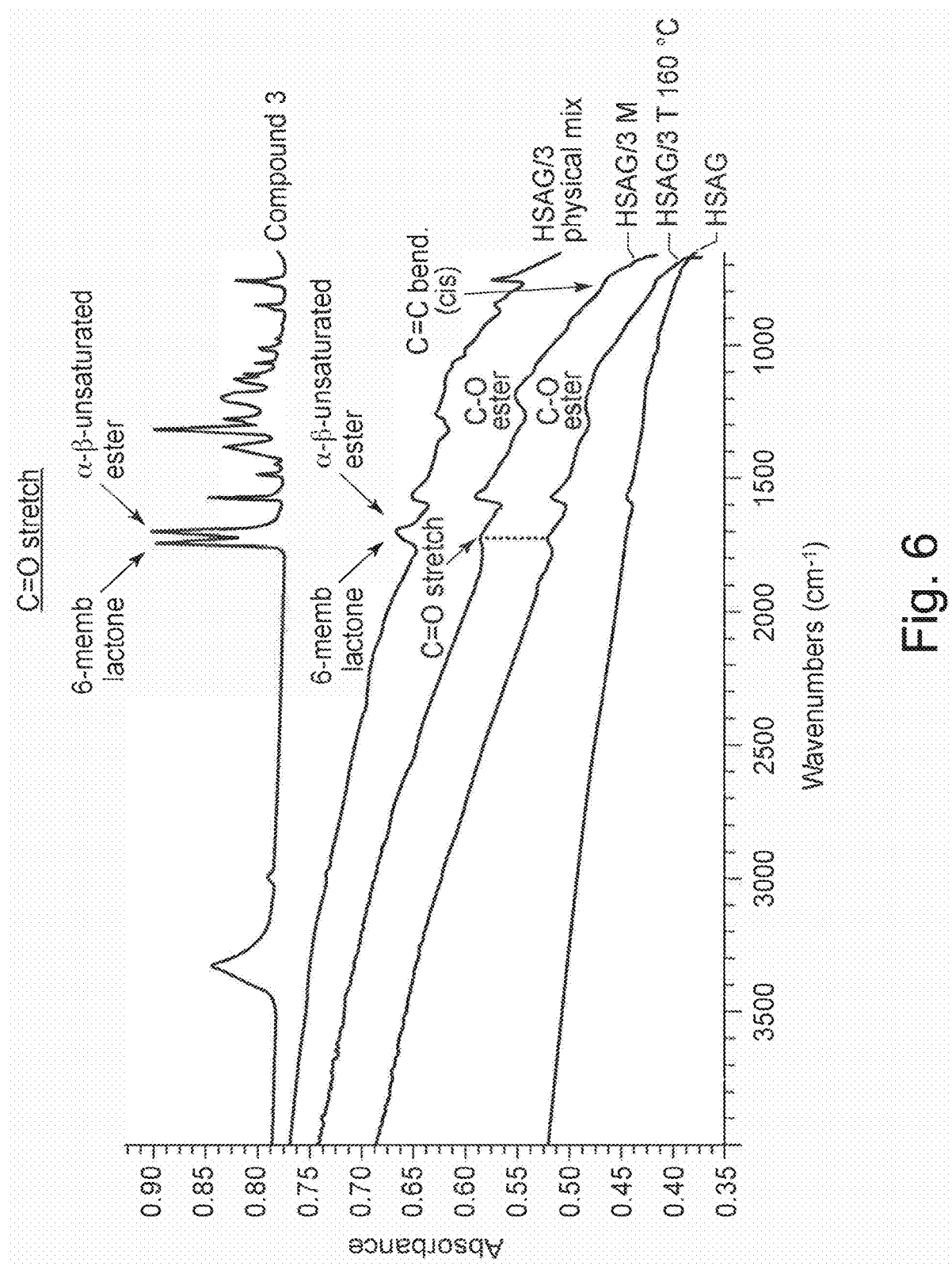
FIG. 6 shows the FT-IR spectra of adducts according to the invention.

FIG. 6 shows the FT-IR spectra of the compound obtained as from example 3, HSAG and of the adducts from examples 4, 12, 11.

All the spectra in FIG. 6 are characterized by increasing absorption at higher wavenumbers due to phenomena of scattering/rereflection of the incident IR light from part of the particles that make up the sample. The FT-IR spectrum of HSAG is characterized by a very intense band at 1569 cm$^{-1}$, relating to the collective C═C stretching vibration typical of the graphene materials. In both spectra of the HSAG/3 T and HSAG/3 adducts, the C═C peak is detectable together with other bands relating to new functional groups. The corresponding peaks are located at: i) 730 cm$^{-1}$, C═C vibrations; ii) 1210 cm$^{-1}$, C—O stretching vibrations and iii) 1729 cm$^{-1}$ C═O.

The spectrum relating to the physical mixture (HSAG/3) shows characteristic bands of pyrone 3 and of the starting graphite. In the spectrum of pyrone 3 there are two very intense bands at 1745 cm$^{-1}$ and 1698 cm$^{-1}$ relating to the stretching vibrations of the two carbonyls (C═O) of pyrone 3. In the spectra of the HSAG/3 adducts, these two bands have disappeared and the presence of a new band is detected at 1729 cm$^{-1}$.

Figure 7:
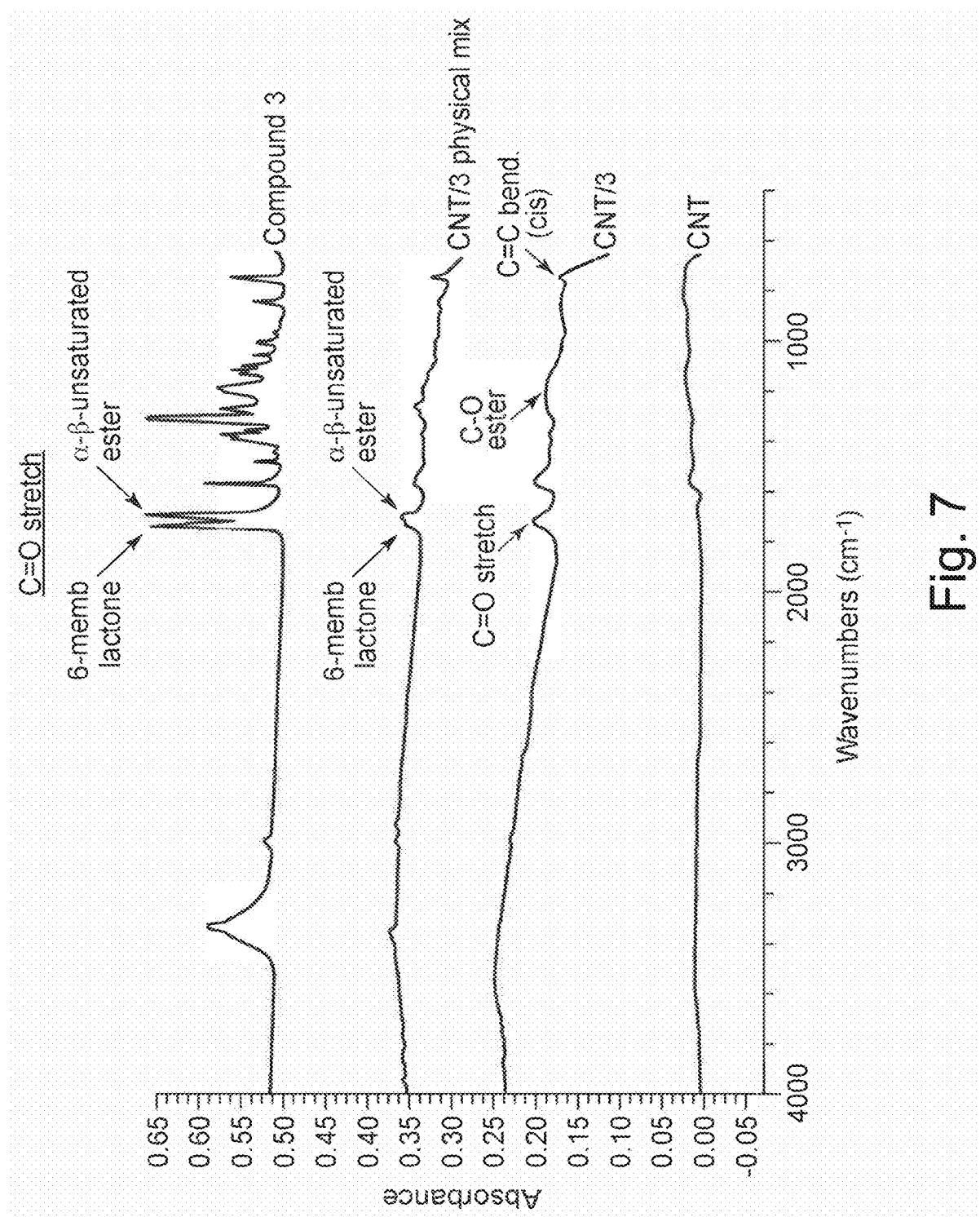
FIG. 7 shows the FT-IR spectra of adducts according to the invention.

FIG. 7 shows the FT-IR spectra of the compound obtained as from example 3, CNT and adducts from examples 13, 14.

All the spectra in FIG. 7 are characterized by increasing absorption at higher wavenumbers due to phenomena of scattering/rereflection of the incident IR light from part of the particles that make up the sample. The FT-IR spectrum of the starting carbon nanotube (CNT) is characterized by a very intense band at 1569 cm$^{-1}$, relating to the collective C=C stretching vibration typical of the graphene materials. In the spectrum of the CNT/3 adduct, the C=C peak is detectable together with other bands relating to new functional groups. The corresponding peaks are located at: i) 730 cm$^{-1}$, C=C vibrations; ii) 1210 cm$^{-1}$, C—O stretching vibration and iii) 1729 cm$^{-1}$ C=O.

The spectrum relating to the physical mixture (CNT/3) shows characteristic bands of pyrone 3 and of the starting graphite. In the spectrum of pyrone 3 there are two very intense bands at 1745 cm$^{-1}$ and 1698 cm$^{-1}$ relating to the stretching vibrations of the two carbonyls (C=O) of pyrone 3. In the spectra of the CNT/3 adducts, these two bands have disappeared and the presence of a new band is detected at 1729 cm$^{-1}$.

Figure 8:
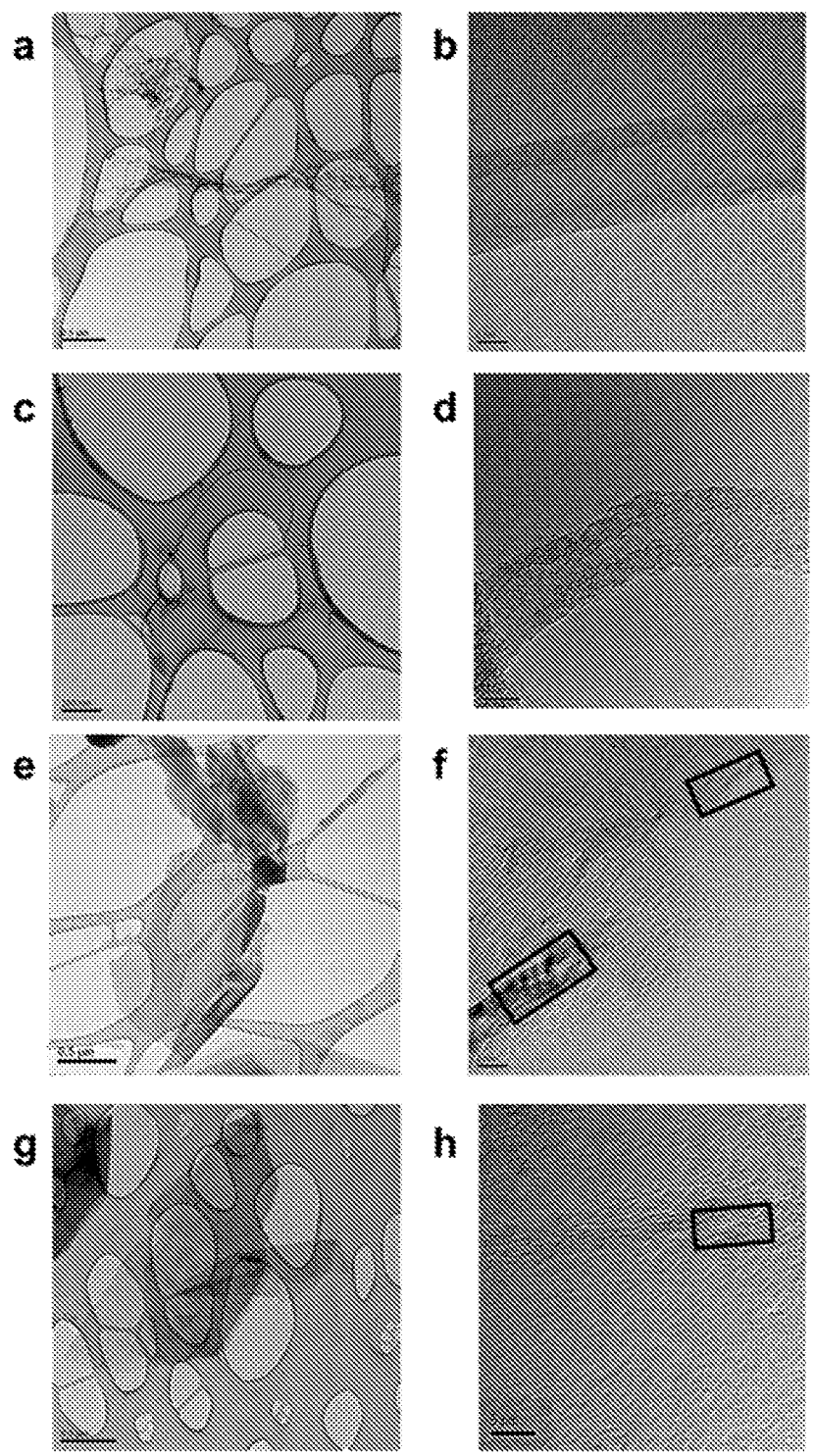
FIG. 8 shows the HRTEM images of adducts according to the invention.

FIG. 8 shows HRTEM images of the CNTs (b), of the adduct from example 13 (d) 11 (f), 12 (h) isolated from the supernatant after centrifugation for 30 min at 6000 rpm. (Bright field TEM micrographs at low magnification (a, c, e, g))

The starting CNTs shown in the figure seem to be agglomerated (entangled) (FIG. 8a). The high-resolution micrographs of the suspensions of CNT 3 adduct show that functionalization seems to improve dispersion of the carbon nanotube in water and seems to promote untangling thereof (FIG. 8c).

In FIG. 8d it can be seen that the surface of the carbon nanotube has been altered considerably after functionalization with compound 3. FIGS. 8e and 8g also show the TEM micrographs relating to the suspensions of the adduct HSAG with compound 3. It appears from the micrographs that the number of stacked graphene sheets has decreased. The micrographs at higher magnification in FIGS. 8f and h reveal the presence of small numbers of superposed graphite layers. It would appear that formation of the HSAG/3 adduct leads to a reduction of the number of stacked layers. In both HSAG/3 adducts it is found that the lateral dimension of the graphene sheets is maintained. FIG. 8f shows nanographites that range from 9 to 20 superposed graphene sheets (indicated in the boxes). In FIG. 8h, we may note the presence of isolated nanographites, in particular with 3 or 4 superposed graphene sheets.

Example 15. Preparation of an Adduct Between the Product of Example 3 and NG24 Graphite (Thermal Treatment at 180° C.)

First the NG24 graphite (1.8 g, 26.2 mmol), the product of example 3 (0.48 g, 2.62 mmol) and acetone (10 ml) are poured into a 100-mL flask. The mixture thus obtained is sonicated for 30 min, using a 2 L bench sonicator. At the end of this time the solvent is removed at reduced pressure. The physical mixture obtained is heated at 180° C. for 3 hours. The powder obtained is washed with acetone (30 mL×3) and then filtered on a Buchner. The final yield of adduct is 75.7%.

Example 16. Preparation of an Adduct Between the Product of Example 3 and NG24 Graphite (Thermal Treatment at 110° C.)

The mixture is prepared as in example 15 but the thermal treatment is carried out at 110° C., with a final yield of adduct of 23%.

Example 17. Preparation of an Adduct Between the Product of Example 3 and NG24 Graphite (Thermal Treatment at 130° C.)

The mixture is prepared as in example 15 but the thermal treatment is carried out at 130° C., with a final yield of adduct of 24%.

Example 18. Preparation of an Adduct Between the Product of Example 3 and NG24 Graphite (Thermal Treatment at 150° C.)

The mixture is prepared as in example 15 but the thermal treatment is carried out at 150° C., with a final yield of adduct of 44%.

Example 19. Preparation of an Adduct Between the Product of Example 3 and NG24 Graphite (Thermal Treatment at 160° C.)

The mixture is prepared as in example 15 but the thermal treatment is carried out at 160° C., with a final yield of adduct of 62.5%.

Example 20. Preparation of an Adduct Between the Product of Example 3 and NG24 Graphite (Thermal Treatment at 200° C.)

The mixture is prepared as in example 15 but the thermal treatment is carried out at 200° C., with a final yield of adduct of 62.9%.

Example 21. Preparation of an Adduct Between the Product of Example 3 and NG24 Graphite (Mechanical Treatment)

The mixture is prepared as in example 15 but the treatment is carried out using a ball mill: planetary ball mill S100 (Retsch) equipped with a jar movable in the horizontal plane (volume=0.3 L). The jar rotated at 300 rpm, at room temperature for 3 hours. The powder thus obtained was purified using acetone (3×30 mL) and filtered on a Buchner. Final yield of adduct=23%.

Example 22. Preparation of an Adduct Between the Product of Example 3 and NG27 Graphite (Thermal Treatment at 160° C.)

The mixture is prepared as in example 15 at a temperature of 160° C. and using NG27 graphite, with a final yield of adduct of 47.5%.

Example 23. Preparation of an Adduct Between the Product of Example 3 and NG27 Graphite (Thermal Treatment at 160° C.)

The mixture is prepared as in example 22 at a temperature of 160° C., using an amount of product of example 3 equal to 3 mol %. Final yield of adduct=72.3%.

Example 24. Preparation of an Adduct Between the Product of Example 3 and NG307 Graphite (Thermal Treatment at 160° C.)

The mixture is prepared as in example 15 at a temperature of 160° C. and using NG307 graphite, with a final yield of adduct of 63.3%.

Example 25. Preparation of an Adduct Between the Product of Example 3 and NG307 Graphite (Thermal Treatment at 160° C.)

The mixture is prepared as in example 24 at a temperature of 160° C., using an amount of product of example 3 equal to 3 mol %. Final yield of adduct=83%.

Example 26. Preparation of an Adduct Between the Product of Example 3 and SFG6 Graphite (Thermal Treatment at 160° C.)

The mixture is prepared as in example 15 at a temperature of 160° C. and using SFG6 graphite, with a final yield of adduct of 3.6%.

Example 27. Preparation of an Adduct Between the Product of Example 3 and G3806 Graphite (Thermal Treatment at 160° C.)

The mixture is prepared as in example 15 at a temperature of 160° C. and using G3806 graphite, with a final yield of adduct of 19.7%.

Example 28. Preparation of an Adduct Between the Product of Example 3 and G3807 Graphite (Thermal Treatment at 160° C.)

The mixture is prepared as in example 15 at a temperature of 160° C. and using G3807 graphite, with a final yield of adduct of 12%.

Example 29. Preparation of an Adduct Between the Product of Example 3 and CB N326 carbon black (thermal treatment at 160° C.)

The mixture is prepared as in example 15 at a temperature of 160° C. and using CB N326 carbon black, with a final yield of adduct of 19.1%.

Example 30. Preparation of an Adduct Between the Product of Example 3 and CB N326 carbon black (thermal treatment at 160° C.)

The mixture is prepared as in example 29 at a temperature of 160° C., using an amount of product of example 3 equal to 3 mol %. Final yield of adduct=50%.

Example 31. Preparation of an Adduct Between the Product of Example 3 and CB N234 carbon black (thermal treatment at 160° C.)

The mixture is prepared as in example 15 at a temperature of 160° C. and using CB N234 carbon black, with a final yield of adduct of 35%.

Example 32. Preparation of an Adduct Between the Product of Example 3 and CB N234 carbon black (thermal treatment at 160° C.)

The mixture is prepared as in example 32 at a temperature of 160° C., using an amount of product of example 3 equal to 3 mol %. Final yield of adduct=62%.

Example 33. Preparation of an Adduct Between the Product of Example 3 and CB N115 carbon black (thermal treatment at 160° C.)

The mixture is prepared as in example 15 at a temperature of 160° C. and using CB N115 carbon black, with a final yield of adduct of 41%.

Example 34. Preparation of an Adduct Between the Product of Example 3 and CB N115 Carbon Black (Thermal Treatment at 160° C.)

The mixture is prepared as in example 33 at a temperature of 160° C., using an amount of product of example 3 equal to 3 mol %. Final yield of adduct=67%.

Examples 35-38

Aqueous Suspensions of Adducts of a Pyrone with Carbon Allotropes

Example 35. Aqueous Suspension of the Product of Example 11, Adduct Between the Product of Example 3 and High Surface Area Graphite (HSAG)

Water is added to an aliquot of the powder obtained in example 11: suspensions at various concentrations were obtained: 1 mg/mL; 0.5 mg/mL; 0.3 mg/mL; 0.1 mg/mL; 0.05 mg/mL; 0.01 mg/mL; 0.05 mg/mL. Each suspension was sonicated for 10 minutes in a 2 L ultrasonic bath (at 260 W) and then UV-Vis absorption was measured immediately after sonication, after 2, 5, 24 hours and 7 days. The suspension at 1 mg/mL (10 mL) was poured into a Falcon™ (15 mL) and centrifuged at 6000 rpm for 30 minutes. The UV-Vis absorption was measured immediately after each centrifugation.

Example 36. Aqueous Suspension of the Product of Example 8, Adduct Between the Product of Example 3 and High Surface Area Graphite (HSAG)

The aqueous suspensions were prepared as described in example 35.

Example 37. Aqueous Suspension of the Product of Example 9, Adduct Between the Product of Example 3 and High Surface Area Graphite (HSAG)

The aqueous suspensions were prepared as described in example 35.

FIGS. 9a-c show UV-VIS measurements of the suspensions prepared as in examples 35, 36 and 37. The Absorbance-Concentration Relation is shown, i.e. the correlation between the absorbance (on the ordinate) and the concentration (on the abscissa).

FIGS. 10a-c show UV-VIS measurements of the suspensions prepared as in examples 35, 36 and 37. The stability over time is shown, i.e.: the absorbance of suspensions that have a concentration equal to 1 mg/mL, measured at different times after sonication.

Example 38. Aqueous Suspension of the Product of Example 14, Adduct Between the Product of Example 3 and Carbon Nanotubes (CNTs)

Water is added to an aliquot of the powder obtained in example 14: suspensions at various concentrations were obtained: 1 mg/mL; 0.5 mg/mL; 0.3 mg/mL; 0.1 mg/mL; 0.05 mg/mL; 0.01 mg/mL; 0.05 mg/mL. Each suspension was sonicated for 10 minutes in a 2 L ultrasonic bath (at 260 W) and then UV-Vis absorption was measured immediately after sonication, after 2, 5, 24 hours and 7 days. FIG. 11 shows UV-VIS measurements of the suspension prepared as in example 38 at 1 mg/mL. In particular, FIG. 11 shows the correlation between absorbance and wavelength, which is typically supplied by a UV-Vis spectrum.

Example 39. Synthesis of the ethyl ester of dihydroxymuconic acid

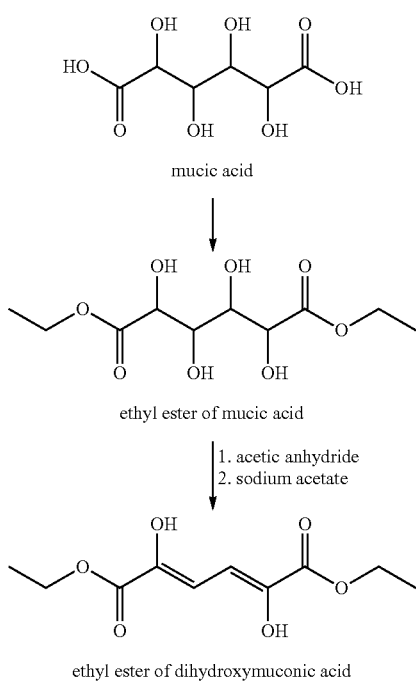

The diester was prepared according to the procedure of Fischer and Speier from mucic acid using anhydrous ethanol and HCl. [Fischer and Speier, Ber., 28, 3252 (1895)]

A 100-mL flask equipped with a magnetic stirrer and a condenser is charged with 10 g of diester of mucic acid and 60 mL of acetic anhydride, in the absence of other chemical individuals. The mixture was stirred at 130° C. overnight. In this first reaction step, the acetic anhydride reacts with the hydroxyls of the ester of mucic acid, causing the acetylation reaction. The acetic anhydride also functions as a solvent. The product is isolated by filtration. Once obtained, the product is poured into a 100-mL flask equipped with a magnetic stirrer and a condenser and 1 g of $CH_3COONa \cdot 3H_2O$ is added. The new reaction mixture is then stirred for 12 hours at 100° C. At the end of this time, HCl solution is added, and a few minutes after addition it is noted that there is formation of a white precipitate. Once formed, the precipitate is removed by filtration.

Example 40. Preparation of an Adduct Between the Product of Example 39 and High Surface Area Graphite (HSAG)

1 g of graphite and 200 mg of the product of example 39 are poured successively into a 100-mL single-neck flask containing 50 mL of acetone. The acetone is then removed at reduced pressure. The mixture is heated at 160° C. for 3 hours. At the end of this treatment, the solid is purified by extraction with acetone in a Soxhlet extractor.

The purified solid was suspended in water (1 mg/1 mL of water). The suspension was sonicated with a bench sonicator for 10 minutes. The suspension proved to be stable for at least 7 days.

Example 41. Synthesis of $N^1,N^6$-dihexyl-2,3,4,5-tetrahydroxyhexanediamide

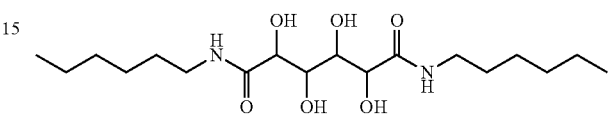

Mucic acid (5 g) and dimethylsulfoxide (10 mL) are poured into a 100-mL single-neck flask. The mixture is stirred at 140° C. for 20 minutes. At the end of this time the mixture is cooled to room temperature. Hexanamine (2 equivalents) is added at this temperature. It is stirred at 100° C. for two hours.

The product is isolated by filtration and is a white solid.

Example 42. Preparation of a Physical Mixture between the Product of Example 41 and High Surface Area Graphite (HSAG)

The graphite and the product of example 41 are poured successively into a 100-mL single-neck flask. Water is added to the mixture and it is sonicated for 30 minutes. The suspension thus obtained proves to be stable for 24 hours.

Example 43 (Comparison). Elastomer Compound with Carbon Black as Reinforcing Filler In the following description, phr signifies parts per hundred rubber, i.e. parts per 100 parts of rubber.

The compound was prepared in an internal mixer of the Brabender® type having a mixing chamber with a volume equal to 50 cc, reaching, with all the ingredients fed in, a degree of filling equal to 80%.

100 phr of natural rubber, commercial grade NR-RSS3, was put in the mixer, and mastication was carried out at 80° C. for 1 minute. Then 60 phr of CB N234 black was added, mixing for a further 5 minutes and discharging the composite obtained at 100° C. The composite thus prepared was then put in the internal mixer at 80° C., adding 2 phr of ZnO (from Zincol Ossidi), 2 phr of stearic acid (from Aldrich), 2 phr of paraphenylenediamine, mixing for 2 minutes. Then 1.20 phr of sulfur (from Solfotecnica) and 1.70 phr of N-tert-butyl-2-benzothiazyl sulfenamide (TBBS) (from Flexsys) were added, mixing for a further 2 minutes. The composite was discharged at 90° C.

Example 44. Elastomer Compound with Adduct According to Example 31 as Reinforcing Filler The compound was prepared according to the preparation in example 43; the carbon black used for preparation had been treated beforehand with the compound prepared in example 3. The procedure for preparing the adduct of CB N234 with the compound prepared in example 3 is as given in example 31.

Dynamic-Mechanical Characterization of the Composites from Examples 43 and 44

Dynamic-mechanical characterization is carried out by the so-called strain sweep test.

The composites of examples 43 and 44 are vulcanized at 151° C. for 30 minutes. The value of the shear storage modulus is then measured, by applying a sinusoidal stress at 50° C. and a frequency of 1 Hz, in a range of strain amplitude between 0.1% and 25%, using the Monsanto R.P.A. 2000 rheometer.

Operating conditions: The specimens were held in the instrument at 50° C. for 90 seconds, the stress was then applied at 50° C. in the range of strain amplitude between 0.1% and 25%, with a frequency of 1 Hz, increasing the strain amplitude in the range stated above. This treatment is carried out to cancel the previous thermo-mechanical history. Application of the stress is then repeated in the same experimental conditions. Vulcanization was then carried out at 150° C. for 30 minutes, with a frequency of 1.667 Hz and an angle of 6.98% (0.5 rad). The vulcanized specimen was left in the instrument for 10 minutes at 50° C. Sinusoidal stress was then applied in the same conditions stated above, then leaving the specimen in the instrument for 10 minutes at 50° C. Sinusoidal stress is then applied again, still in the same experimental conditions. Table 1 shows the values of $G'_{\gamma=0.28\%}$, $\Delta G'$, $G''_{max}$ and $(Tan\ Delta)_{max}$ determined by the strain sweep test for the composites of Example 43 and of Example 44. The values presented in Table 1 demonstrate that there is a reduction of the Payne effect of the composite when a carbon black modified with a compound according to the invention is used.

TABLE 1

| Example of preparation of compound | | Ex. 43 | Ex. 44 |
| --- | --- | --- | --- |
| $G'_{\gamma=0.28\%}$ | MPa | 6.58 | 5.85 |
| $\Delta G'$ | MPa | 4.98 | 4.25 |
| $G''_{max}$ | MPa | 0.85 | 0.71 |
| $(Tan\ Delta)_{max}$ | — | 0.27 | 0.24 |

$G'_{\gamma=0.28\%}$ = value of G' measured at 0.28%. $\Delta G'$ = difference between the value of G' at minimum strain and the value of G' measured at the maximum strain reached. $G''_{max}$ = maximum value of G'' observed on the curve of G''. $(Tan\ Delta)_{max}$ = maximum value of Tan Delta observed on the curve.

The invention claimed is:

1. An elastomer composition comprising an adduct between an $sp^2$ hybridized carbon allotrope and a compound of formula (I)

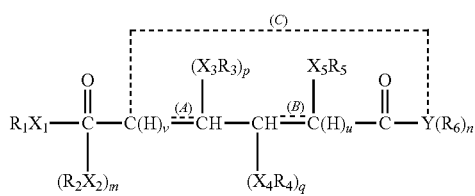

(I)

wherein the compound of formula (I) may be linear or cyclic and the symbol (C) does not represent a bond when the compound is linear and represents a bond when the compound is cyclic, and $X_1$, $X_2$, $X_3$, $X_4$, $X_5$ are selected independently from the group consisting of O, N—$R_7$, halogen and S;

and wherein if $X_1$, $X_2$, $X_3$, $X_4$, $X_5$ are halogen, $R_1$, $R_2$, $R_3$, $R_4$, $R_5$ are absent;

and wherein:

the compound of formula (I) is linear when:

m and n are 1 and Y is selected from the group consisting of O, N—$R_7$ and S; or m is 1 and n is 0 and Y is halogen and when the compound is linear, the symbols (A) and (B) represent independently a single or a double bond, and if the symbols (A) and (B) are a double bond, v, u, p and q are 0;

if the symbols (A) and (B) are a single bond, v, u, p, q are 1;

if the symbol (A) is a double bond and the symbol (B) is a single bond, v and p are 0 whereas u and q are 1;

if the symbol (B) is a double bond and the symbol (A) is a single bond, v and p are 1 whereas u and q are 0;

the compound of formula (I) is cyclic when:

the symbols (A) and (B) are a double bond, and m, v, p, q and u are 0, and if Y is O, n is 0, or if Y is N, n is 1;

and wherein:

if $X_1$ and Y are $NR_7$ or S, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ and Y are O, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

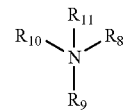

in which $R_8$, $R_9$, $R_{10}$, $R_{11}$ are selected independently from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_2$ $X_3$, $X_4$, $X_5$ are O, $NR_7$ or S, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_2$, $R_3$, $R_4$, $R_5$ are selected independently from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

2. The elastomer composition as claimed in claim 1, in which the compound of formula (I) is represented by formula (II)

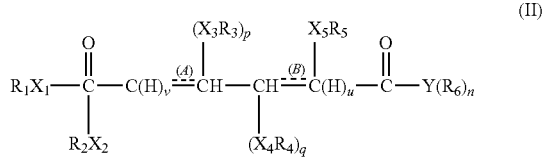

in which $X_1$, $X_2$, $X_3$, $X_4$, $X_5$ are selected independently from the group consisting of O, N—$R_7$, halogen and S;

and in which if $X_1$, $X_2$, $X_3$, $X_4$, $X_5$ are halogen, $R_1$, $R_2$, $R_3$, $R_4$, $R_5$ are absent;

and in which if n is 1, Y is selected from the group consisting of O, N—$R_7$ and S; or if n is 0, Y is halogen, and in which the symbols (A) and (B) represent independently a single or a double bond, and if the symbols ((A) and (B) are a double bond, v, p, u and q are 0, whereas if the symbols (A) and (B) are a single bond, v, p, q are 1; and if the symbol (A) is a double bond and the symbol (B) is a single bond, v and p are 0 whereas u and q are 1;

if the symbol (B) is a double bond and the symbol (A) is a single bond, v and p are 1 whereas u and q are 0;

and in which:

if $X_1$ and Y are $NR_7$ or S, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ and Y are O, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

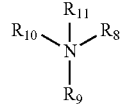

in which $R_8$, $R_9$, $R_{10}$, $R_{11}$ are selected independently from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_2$ $X_3$, $X_4$, $X_5$ are O, $NR_7$ or S, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_2$, $R_3$, $R_4$, $R_5$ are selected independently from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

3. The elastomer composition as claimed in claim 1, in which the compound of formula (I) is represented by formula (III)

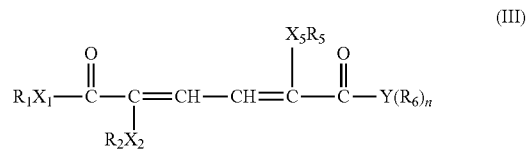

in which $X_1$, $X_2$, $X_5$ are selected independently from the group consisting of O, N—$R_7$, halogen and S;

and in which if $X_1$, $X_2$, $X_5$ are halogen, $R_1$, $R_2$, $R_5$ are absent;

and if n is 1, Y is selected from the group consisting of O, N—$R_7$ and S; or if n is 0, Y is halogen and in which:

if $X_1$ and Y are $NR_7$ or S, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ and Y are O, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

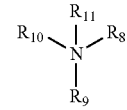

in which $R_8$, $R_9$, $R_{10}$, $R_{11}$ are selected independently from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_2$ or $X_5$ are O, $NR_7$ or S, then:

$R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_2$, $R_5$ are selected independently from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

4. The elastomer composition as claimed in claim 1, in which the compound of formula (I) is represented by formula (IV)

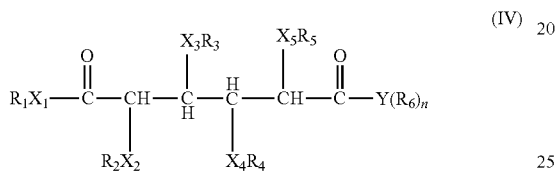

in which $X_1$, $X_2$, $X_3$, $X_4$, $X_5$ are selected independently from the group consisting of O, N—$R_7$, halogen and S;

and in which if $X_1$, $X_2$, $X_3$, $X_4$, $X_5$ are halogen, $R_1$, $R_2$, $R_3$, $R_4$, $R_5$ are absent;

and in which if n is 1, Y is selected from the group consisting of O, N—$R_7$ and S; or if n is 0, Y is halogen and in which:

if $X_1$ and Y are $NR_7$ or S, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ and Y are O, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

in which $R_8$, $R_9$, $R_{10}$, $R_{11}$ are selected independently from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_2$, $X_3$, $X_4$, $X_5$ are O, $NR_7$ or S, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_2$, $R_3$, $R_4$, $R_5$ are independently selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

5. The elastomer composition as claimed in claim 1, wherein the compound of formula (I) is represented by formula (V)

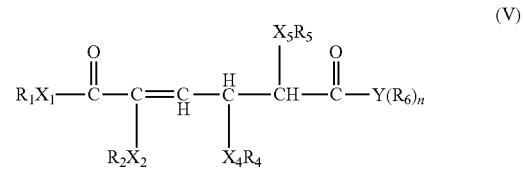

wherein $X_1$, $X_2$, $X_4$, $X_5$ are selected independently from the group consisting of O, N—$R_7$, halogen and S;

and wherein if $X_1$, $X_2$, $X_4$, $X_5$ are halogen, $R_1$, $R_2$, $R_4$, $R_5$ are absent;

and wherein if n is 1 and Y is selected from the group consisting of O, N—$R_7$ and S; or if n is 0 and Y is halogen and wherein:

if $X_1$ and Y are $NR_7$ or S, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ and Y are O, then:
  $R_1$, $R_6$ are selected independently from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

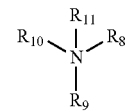

wherein $R_8$, $R_9$, $R_{10}$, $R_{11}$ are independently selected from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_2$, $X_4$, $X_5$ are O, $NR_7$ or S, then:
  $R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_2$, $R_4$, $R_5$ are independently selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

6. The elastomer composition as claimed in claim 1, in which the compound of formula (I) is represented by formula (VI)

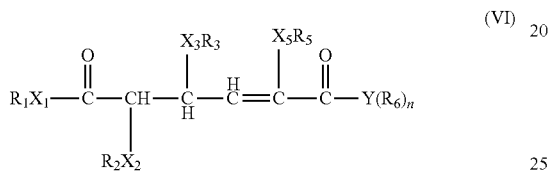

(VI)

wherein $X_1$, $X_2$, $X_3$, $X_5$ are selected independently from the group consisting of O, N—$R_7$, halogen and S;

wherein if $X_1$, $X_2$, $X_3$, $X_5$ are halogen, $R_1$, $R_2$, $R_3$, $R_5$ are absent;

and wherein if n is 1 and Y is selected from the group consisting of: O, N—$R_7$ and S; or if n is 0 and Y is halogen, and in which:

if $X_1$ and Y are $NR_7$ or S, then:
$R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ and Y are O, then:
$R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

in which $R_8$, $R_9$, $R_{10}$, $R_{11}$ are independently selected from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_2$, $X_3$, $X_5$ are O, $NR_7$ or S, then:
$R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_2$, $R_3$, $R_5$ are independently selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

7. The elastomer composition as claimed in claim 1, in which the compound of formula (I) is represented by formula (VII)

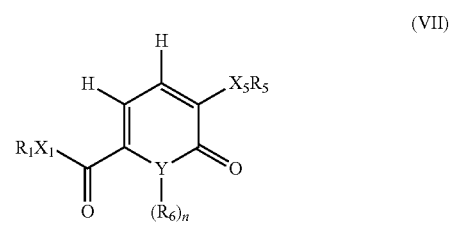

(VII)

wherein $X_1$, $X_3$, $X_4$, $X_5$ are selected independently from the group consisting of: O, N—$R_7$, halogen and S;

wherein if $X_1$, $X_3$, $X_4$, $X_5$ are halogen, $R_1$, $R_3$, $R_4$, $R_5$ are absent;

if Y is O, n is 0, or if Y is N, n is 1;

and wherein:

if $X_1$ is $NR_7$ or S, then:
$R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_1$ is O, then:
$R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl, alkali metals, alkaline-earth metals, transition metals, or

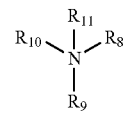

in which $R_8$, $R_9$, $R_{10}$, $R_{11}$ are independently selected from the group consisting of: hydrogen, linear or branched $C_1$-$C_6$ alkyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

if $X_3$, $X_4$, $X_5$ are O, $NR_7$ or S, then:
$R_1$, $R_6$ are independently selected from the group consisting of: hydrogen, linear or branched $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl;

$R_3$, $R_4$, $R_5$ are independently selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl; and $R_7$ is selected from the group consisting of: hydrogen, $C_2$-$C_6$ acyl, $C_1$-$C_6$ alkyl, linear or branched $C_2$-$C_6$ alkenyl or alkynyl, aryl, linear or branched $C_1$-$C_6$ alkyl-aryl, linear or branched $C_2$-$C_6$ alkenyl-aryl, linear or branched $C_2$-$C_6$ alkynyl-aryl, heteroaryl.

8. The elastomer composition as claimed in claim 1, wherein said $sp^2$ hybridized carbon allotrope is selected from the group consisting of: carbon black, fullerene, single-wall or multi-walled carbon nanotubes, graphene, graphite with a number of graphene sheets between 2 and 10000.

9. The elastomer composition as claimed in claim 1, wherein said carbon allotrope comprises functional groups selected from the group consisting of:

oxygenated functional groups, preferably hydroxyls, epoxides;

functional groups containing carbonyls, preferably aldehydes, ketones, carboxylic acids;

functional groups containing nitrogen atoms, preferably amines, amides, nitriles, diazonium salts, imines;

functional groups containing sulfur atoms, preferably sulfides, disulfides, mercaptans, sulfones, sulfinic and sulfonic groups.

10. The elastomer composition as claimed in claim 9, wherein said carbon allotrope is graphite oxide.

11. The elastomer composition as claimed in claim 9, wherein said carbon allotrope is graphene oxide.

12. The elastomer composition as claimed in claim 1, wherein said compound of formula (I) is in the form of a salt and said alkali metals are selected from the group consisting of lithium, sodium, potassium; said alkaline-earth metals are selected from the group consisting of magnesium, calcium; said transition metals are rare earths, preferably neodymium.

\* \* \* \* \*